(12) United States Patent
Popp

(10) Patent No.: US 10,336,983 B2
(45) Date of Patent: Jul. 2, 2019

(54) METHOD FOR INCREASING THE SPECIFIC PRODUCTION RATE OF EUKARYOTIC CELLS

(71) Applicant: Hoffmann-La Roche Inc., Little Falls, NJ (US)

(72) Inventor: Oliver Popp, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/428,279

(22) Filed: Feb. 9, 2017

(65) Prior Publication Data

US 2017/0152473 A1 Jun. 1, 2017

Related U.S. Application Data

(63) Continuation of application No. PCT/EP2015/067733, filed on Jul. 31, 2015.

(30) Foreign Application Priority Data

Aug. 11, 2014 (EP) .................................... 14180586

(51) Int. Cl.
*C12P 21/00* (2006.01)
*C12N 5/00* (2006.01)
*C12N 5/071* (2010.01)

(52) U.S. Cl.
CPC ......... *C12N 5/0018* (2013.01); *C12N 5/0025* (2013.01); *C12N 5/0682* (2013.01); *C12N 2500/32* (2013.01); *C12N 2500/33* (2013.01); *C12N 2501/998* (2013.01); *C12N 2510/02* (2013.01)

(58) Field of Classification Search
None
See application file for complete search history.

(56) References Cited

PUBLICATIONS

Bertin et al (PNAS, 2007, Col.104, No. 43, pp. 16964-16969).*
Ruggiero et al (Cancer Research, 2011, vol. 71, No. 22, pp. 7113-7124).*
Bridges et al., "Hypermutation in bacteria and other cellular systems" Philos Trans R Soc Lond B Biol Sci 356(29-39) ( 2001).
Wen et al, "Discovery and Investigation of Misincorporation of Serine at Asparagine Positions in Recombinant Proteins Expressed in Chinese Hamster Ovary Cells" J Biol Chem 284:32686-32694 ( 2009).
Feeney et al., "Eliminating Tyrosine Sequence Variants in CHO Cell Lines Producing Recombinant Monoclonal Antibodies" Biotechnology and Bioengineering 110:1087-1097 (2013).
Gurer-Orhan, H. et al., "Misincorporation of free m-tyrosine into cellular proteins: a potential cytotoxic mechanism for oxidized amino acids" Biochem. J. 395(2):277-284 ( 2006).
Han et al., "Enhanced Interferon-β Production by CHO Cells Through Elevated Osmolality and Reduced Culture Temperature" Biotechnol Prog. 25:1440-1447 ( 2009).
ISR for PCT/EP2015/067733 (dated Oct. 27, 2015).
Jakubowski et al., "Translational Accuracy of Aminoacyl-tRNA Synthetases: Implications for Atherosclerosis" The Journal of Nutrition 131:2983S-2987S ( 2001).
Khetan et al., "Control of Misincorporation of Serine for Asparagine During Antibody Production Using CHO Cells" Biotechnology and Bioengineering 107:116-123 ( 2010).
Lee et al., "Histone deacetylase inhibitors decrease proliferation potential and multilineage differentiation capability of human mesenchymal stem cells" Cell Proliferation 42:711-720 (2009).
McMurray-Beaulieu, V. et al., "Na-butyrate sustains energetic status of metabolism and t-PA productivity of CHO cells" Journal of Bioscience and Bioengineering 108(2):160-167 ( 2009).
Yoon et al., "Effect of Culture pH on Erythropoietin Production by Chinese Hamster Ovary Cells Grown in Suspension at 32.5 and 37.0° C" Biotechnology and Bioengineering 89:345-356 (2005).
Zeck et al., "Low Level Sequence Variant Analysis of Recombinant Proteins: An Optimized Approach" 7:e40328 ( 2012).

* cited by examiner

*Primary Examiner* — Celine X Qian
(74) *Attorney, Agent, or Firm* — Steven Cui

(57) ABSTRACT

The current invention reports the use of meta-tyrosine for increasing the specific productivity of a eukaryotic cell that produces/expresses a polypeptide. In the current method it is not necessary to perform a temperature-, osmolality- or pH shift or to add drugs like valproic acid or sodium butyrate to modulate the specific productivity of the cultivated cells. The method does not affect cell viability or product titer.

11 Claims, 17 Drawing Sheets

METHOD FOR INCREASING THE SPECIFIC PRODUCTION RATE OF EUKARYOTIC CELLS

CROSS REFERENCE TO RELATED APPLICATIONS

This application is a continuation of International Patent Application No. PCT/EP2015/067733 having an international filing date of Jul. 31, 2015, the entire contexts of which are incorporated herein by reference, and which claims benefit under 35 U.S.C. 119 to European Patent Application No. 14180586.1 filed on Aug. 11, 2014.

FIELD OF THE INVENTION

The current invention is in the field of polypeptide production and cell culture media. Herein reported is the use of a meta-tyrosine in a cell culture medium for increasing specific productivity (qP), a process for producing a polypeptide in a cell culture medium comprising meta-tyrosine and a cell culture medium comprising meta-tyrosine.

BACKGROUND OF THE INVENTION

Cell cultures are used in fermentative processes to produce substances, in particular proteins. A distinction is made between processes in which the cell cultures are genetically unmodified and form their own metabolic products and processes in which the organisms are genetically modified in such a manner that they either produce a larger amount of their own substances such as proteins or produce foreign (heterologous) substances. The organisms producing the substances are supplied with a nutrient medium which guarantees the survival of the organisms and enables the production of the desired target compound. Numerous culture media are known for these purposes which enable an optimal cultivation of the specific host.

Protein biotherapeutics, like monoclonal antibodies, are considered as well-established drugs to treat serious illnesses and disease, such as cancer, multiple sclerosis and rheumatoid arthritis (see review from Leader et al. (Leader et al. 2008)). Critical molecular quality attributes of these highly active compounds have to be tightly monitored to ensure patient safety and functional efficacy. Unintended chemical modifications of the target protein can occur during whole production process starting from synthesis by microorganisms and cell cultures, during protein purification, formulation and storage. The most commonly observed chemical degradation pathways for protein pharmaceuticals are asparagine deamidation, aspartate isomerization (Wakankar and Borchardt, 2006; Diepold et al. 2012; Dengl et al. 2013), and oxidation (Li et al. 1995; Ji et al. 2009; Hensel et al. 2011). Recently, several studies reported an additional relevant yet enzyme-generated byproduct, so-called protein SV of recombinantly synthesized biotherapeutics (Khetan et al. 2010; Wen et al. 2009; Feeney et al. 2013). SVs are unintended amino acid replacements at genetically anticipated positions which originate either from intrinsic nucleotide mutations (Bridges, 2001) or alternative amino acid misincorporation during translation (Zeck et al. 2012). Translational misincorporation is thought to be caused by promiscuity of aminoacyl-tRNA synthetase (aaRS) for structurally related amino acids in the course of endogen substrate limitation (Feeney et al. 2013; Jakubowski, 2001). Misincorporation of free meta-tyrosine into cellular proteins as a potential cytotoxic mechanism for oxidized amino acids is reported in Gurer-Urhan et. al., (2006).

SUMMARY OF THE INVENTION

It has been found that supplementation of a culture medium with meta-tyrosine provides for an increased specific productivity (qP) of a eukaryotic (host) cell which produces a (non-endogenous) polypeptide. It has been found that the addition of meta-tyrosine to a cultivation of eukaryotic cells does not lead to a significant decrease in cell viability or final product titer. Cell growth in such a cultivation is reduced/affected in a negative manner (represented by reduced viable cell density (VCD) and overall biomass production (indicated as CTI)). In the current method it is not necessary to perform a temperature-, osmolality- or pH shift to increase the specific productivity of the cultivated cells. It is also not necessary to modulate the specific productivity by addition of drugs like valproic acid or sodium butyrate. The occurrence of amino acid sequence variants (SVs) due to alternative amino acid misincorporation during mRNA translation in the presence of meta-tyrosine is controlled by additional feeding of phenylalanine in non-limiting concentrations.

One aspect as reported herein is the use of meta-tyrosine for increasing the specific productivity of a eukaryotic host cell that produces/expresses/secretes a (non-endogenous/exogenous) polypeptide.

In one embodiment of this aspect the eukaryotic host cell is a mammalian cell. In one embodiment of this aspect the eukaryotic host cell is a Chinese Hamster Ovary (CHO) cell. In one embodiment of this aspect the CHO cell is an in suspension growing CHO cell/cell line (=a CHO suspension cell/cell line). In one embodiment of this aspect the CHO cell is a CHO-K1 cell.

In one embodiment of this aspect the meta-tyrosine is added to result at a (final) concentration of from 0.2 mM to 0.7 mM. In one embodiment of this aspect the meta-tyrosine is added to result at a (final) concentration of from 0.25 mM to 0.6 mM. In one embodiment of this aspect the meta-tyrosine is added to result at a (final) concentration of from 0.3 mM to 0.5 mM. In one embodiment of this aspect the meta-tyrosine is added to result at a (final) concentration of from 0.3 mM to 0.4 mM.

In one embodiment of this aspect the specific productivity is increased by at least 5% compared to an identical production process without supplementation of meta-tyrosine. In one embodiment of this aspect the specific productivity is increased by at least 10% compared to an identical production process without supplementation of meta-tyrosine. In one embodiment of this aspect the specific productivity is increased by at least 20% compared to an identical production process without supplementation of meta-tyrosine. In one embodiment of this aspect the specific productivity is increased by at least 25% compared to an identical production process without supplementation of meta-tyrosine.

In one embodiment of this aspect the use is in a protein-free culture medium. In one embodiment of this aspect the use is in a chemically defined culture medium. In one embodiment of this aspect the use is in a protein-free, chemically defined culture medium.

In one embodiment of this aspect the use is in a culture medium that additionally comprises phenylalanine in a non-limiting concentration. In one embodiment of this aspect the use is in a culture medium that additionally comprises phenylalanine in a non-limiting concentration, wherein phenylalanine is added by continuous feeding or by one or more individual bolus shots of Phe stock solutions at the beginning or during the fermentation process.

In one embodiment of this aspect the molar ratio of/for meta-tyrosine/phenylalanine is lower than or equal to 1.25. In one embodiment of this aspect the final protein sequence fidelity with respect to Phe→m-Tyr misincorporation is higher than or equal to 95.0%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 95.0%. This means that 5% or less meta-tyrosine residues are misincorporated over correctly incorporated phenylalanine residues into the protein sequence. In one embodiment of this aspect the molar ratio of/for meta-tyrosine/phenylalanine is lower than or equal to 0.25. In one embodiment of this aspect the final protein sequence fidelity with respect to Phe→m-Tyr misincorporation is higher than or equal to 99.0%. In one embodiment of this aspect the molar ratio of/for meta-tyrosine/phenylalanine is lower than or equal to 0.25 and the final protein sequence fidelity with respect to Phe→m-Tyr misincorporation is higher than or equal to 99.0%. In one embodiment of this aspect the molar ratio of/for meta-tyrosine/phenylalanine is lower than or equal to 0.125. In one embodiment of this aspect the final protein sequence fidelity with respect to Phe→m-Tyr misincorporation is higher than or equal to 99.5%. In one embodiment of this aspect the molar ratio of/for meta-tyrosine/phenylalanine is lower than or equal to 0.125 and the final protein sequence fidelity with respect to Phe→m-Tyr misincorporation is higher than or equal to 99.5%. In one embodiment of this aspect the molar ratio of/for meta-tyrosine/phenylalanine is lower than or equal to 0.025. In one embodiment of this aspect the final protein sequence fidelity with respect to Phe→m-Tyr misincorporation is higher than or equal to 99.9%. In one embodiment of this aspect the molar ratio of/for meta-tyrosine/phenylalanine is lower than or equal to 0.025 and the final protein sequence fidelity with respect to Phe→m-Tyr misincorporation is higher than or equal to 99.9%.

In one embodiment of this aspect the use is at a constant temperature.

In one embodiment of this aspect the use is at a temperature which is reduced in the course of the use.

In one embodiment of this aspect the use is at a constant pH.

In one embodiment of this aspect the polypeptide is an immunoglobulin or a variant thereof or a fragment thereof or a fusion thereof. In one embodiment of this aspect the polypeptide is a human or humanized immunoglobulin or a variant thereof or a fragment thereof or a fusion thereof. In one embodiment of this aspect the polypeptide is a humanized antibody. In one embodiment of this aspect the polypeptide is a humanized monoclonal antibody.

One aspect as reported herein is a process for producing a polypeptide in a eukaryotic host cell expressing a nucleic acid encoding the polypeptide, comprising culturing the eukaryotic host cell in a culture medium comprising meta-tyrosine.

In one embodiment of this aspect the meta-tyrosine is added to result at a (final) concentration of from 0.2 mM to 0.7 mM. In one embodiment of this aspect the meta-tyrosine is added to result at a (final) concentration of from 0.25 mM to 0.6 mM. In one embodiment of this aspect the meta-tyrosine is added to result at a (final) concentration of from 0.3 mM to 0.5 mM. In one embodiment of this aspect the meta-tyrosine is added to result at a (final) concentration of from 0.3 mM to 0.4 mM.

In one embodiment of this aspect the specific productivity is increased by at least 5% compared to an identical production process without supplementation of meta-tyrosine. In one embodiment of this aspect the specific productivity is increased by at least 10% compared to an identical production process without supplementation of meta-tyrosine. In one embodiment of this aspect the specific productivity is increased by at least 20% compared to an identical production process without supplementation of meta-tyrosine. In one embodiment of this aspect the specific productivity is increased by at least 25% compared to an identical production process without supplementation of meta-tyrosine.

In one embodiment of this aspect the eukaryotic host cell is a mammalian cell. In one embodiment of this aspect the eukaryotic host cell is a Chinese Hamster Ovary (CHO) cell. In one embodiment of this aspect the CHO cell is a CHO suspension cell/a CHO cell growing in suspension. In one embodiment of this aspect the CHO cell is a CHO-K1 cell.

In one embodiment of this aspect the process is performed in a protein-free culture medium. In one embodiment of this aspect the process is performed in a chemically defined culture medium. In one embodiment of this aspect the process is performed in a protein-free, chemically defined culture medium.

In one embodiment of this aspect the process is performed in a culture medium that additionally comprises phenylalanine in a non-limiting concentration. In one embodiment of this aspect the process is performed in a culture medium that additionally comprises phenylalanine in a non-limiting concentration, wherein phenylalanine is added by continuous feeding or by one or more individual bolus shots of Phe stock solutions at the beginning or during the fermentation process.

In one embodiment of this aspect the molar ratio of/for meta-tyrosine/phenylalanine is lower than or equal to 1.25. In one embodiment of this aspect the final protein sequence fidelity with respect to Phe→m-Tyr misincorporation is higher than or equal to 95.0%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 95.0%. This means that 5% or less meta-tyrosine residues are misincorporated over correctly incorporated phenylalanine residues into the protein sequence.

In one embodiment of this aspect the molar ratio of/for meta-tyrosine/phenylalanine is lower than or equal to 0.25. In one embodiment of this aspect the final protein sequence fidelity with respect to Phe→m-Tyr misincorporation is higher than or equal to 99.0%. In one embodiment of this aspect the molar ratio of/for meta-tyrosine/phenylalanine is lower than or equal to 0.25 and the final protein sequence fidelity with respect to Phe→m-Tyr misincorporation is higher than or equal to 99.0%.

In one embodiment of this aspect the molar ratio of/for meta-tyrosine/phenylalanine is lower than or equal to 0.125. In one embodiment of this aspect the final protein sequence fidelity with respect to Phe→m-Tyr misincorporation is higher than or equal to 99.5%. In one embodiment of this aspect the molar ratio of/for meta-tyrosine/phenylalanine is lower than or equal to 0.125 and the final protein sequence fidelity with respect to Phe→m-Tyr misincorporation is higher than or equal to 99.5%.

In one embodiment of this aspect the molar ratio of/for meta-tyrosine/phenylalanine is lower than or equal to 0.025. In one embodiment of this aspect the final protein sequence fidelity with respect to Phe→m-Tyr misincorporation is higher than or equal to 99.9%. In one embodiment of this aspect the molar ratio of/for meta-tyrosine/phenylalanine is lower than or equal to 0.025 and the final protein sequence fidelity with respect to Phe→m-Tyr misincorporation is higher than or equal to 99.9%.

In one embodiment of this aspect the process is performed at a constant temperature. In one embodiment of this aspect the process is performed at a temperature which is reduced in the course of the use.

In one embodiment of this aspect the process is performed at a constant pH.

In one embodiment of this aspect the polypeptide is an immunoglobulin or a variant thereof or a fragment thereof or a fusion thereof. In one embodiment of this aspect the polypeptide is a human or humanized immunoglobulin or a variant thereof or a fragment thereof or a fusion thereof. In one embodiment of this aspect the polypeptide is a humanized antibody. In one embodiment of this aspect the polypeptide is a humanized monoclonal antibody.

One aspect as reported herein is a culture medium comprising meta-tyrosine and phenylalanine in a molar ratio which is lower than or equal to 1.25. One aspect as reported herein is a culture medium comprising meta-tyrosine and phenylalanine in a molar ratio which is lower than or equal to 1.25 and the final protein sequence fidelity with respect to Phe→m-Tyr misincorporation is higher than or equal to 95.0%. This means that 5% or less meta-tyrosine residues are misincorporated over correctly incorporated phenylalanine residues into the protein sequence.

One aspect as reported herein is a culture medium comprising meta-tyrosine and phenylalanine in a molar ratio which is lower than or equal to 0.25. One aspect as reported herein is a culture medium comprising meta-tyrosine and phenylalanine in a molar ratio which is lower than or equal to 0.25 and the final protein sequence fidelity with respect to Phe→m-Tyr misincorporation is higher than or equal to 99.0%.

One aspect as reported herein is a culture medium comprising meta-tyrosine and phenylalanine in a molar ratio which is lower than or equal to 0.125. One aspect as reported herein is a culture medium comprising meta-tyrosine and phenylalanine in a molar ratio which is lower than or equal to 0.125 and the final protein sequence fidelity with respect to Phe→m-Tyr misincorporation is higher than or equal to 99.5%.

One aspect as reported herein is a culture medium comprising meta-tyrosine and phenylalanine in a molar ratio which is lower than or equal to 0.025. One aspect as reported herein is a culture medium comprising meta-tyrosine and phenylalanine in a molar ratio which is lower than or equal to 0.025 and the final protein sequence fidelity with respect to Phe→m-Tyr misincorporation is higher than or equal to 99.9%.

In one embodiment of this aspect the culture medium is a protein-free culture medium. In one embodiment of this aspect the culture medium is a chemically defined culture medium. In one embodiment of this aspect the culture medium is a protein-free, chemically defined culture medium.

DETAILED DESCRIPTION OF THE INVENTION

Modulation of the specific productivity (qP) of a eukaryotic cell is thought to be a powerful tool to address alterations in product quality attributes such as micro heterogeneity in protein N-glycosylation, charge variants, protein aggregates and fragments profiles. For example, moderate qP is supposed to support posttranslational N-glycosylation since the target protein may have a longer residence time in glycan formation compartments endoplasmatic reticulum (ER) and Golgi apparatus (Hossler et al. 2009).

Currently, modulation of qP in biotechnological practice is realized either by drugs like the histone deacetylase (HDAC) inhibitors valproic acid and sodium butyrate (Lee et al. 2009; Murray-Beaulieu et al. 2009) or by chemico-physical parameters such temperature shift (Hendrick et al. 2001), pH shift (Yoon et al. 2005), and increase of osmolality (Han et al. 2009). These approaches have significant drawbacks. HDAC inhibitors on the one hand severely decrease cell viability and induce apoptosis which may cause secondary problems like target protein fragmentation and poor host cell protein and DNA elimination performance during protein purification. On the other hand, chemico-physical parameters are hard to control in GMP facilities and often vary in shift kinetics of different bioreactors due to vessel limitations and different mass transfers. Herein is reported that the specific supplementation of meta-tyrosine to biotechnological processes is a promising alternative to existing procedure to increase qP of eukaryotic cells, especially CHO cells, without affecting cell viability and without the need of chemico-physical adjustments.

However, it has been reported by Gurer-Orhan et al., (2006) that certain levels of meta-tyrosine concentrations induce cytotoxic effects in adherently growing CHO cells.

The invention as reported herein is at least in part based on the finding that the supplementation of a culture medium with meta-tyrosine leads to an increased specific productivity (qP) of a eukaryotic, especially a CHO, suspension cell which produces an exogenous polypeptide.

Contrary to finding of Gurer-Orhan et al. the addition of meta-tyrosine does not lead to cytotoxic effects (i.e. cell viability and final product titer are not significantly affected), although cell growth is affected in a negative manner as can be seen by the reduced viable cell density (VCD) and overall biomass production (indicated as CTI) (see FIGS. 1 to 5).

Hence, one aspect as reported herein is the use of meta-tyrosine for increasing the specific productivity of a eukaryotic host cell that produces a polypeptide.

One aspect as reported herein is a process for producing a polypeptide in a eukaryotic host cell expressing a nucleic acid encoding the polypeptide, comprising culturing the eukaryotic host cell in a culture medium comprising meta-tyrosine.

In one embodiment of all aspects the eukaryotic host cell is a mammalian cell. In one embodiment the mammalian cell is selected from the mammalian cells comprising CHO cells (e.g. CHO-K1 or CHO DG44), BHK cells, NS0 cells, SP2/0 cells, HEK 293 cells, HEK 293 EBNA cells, PER.C6 cells, and COS cells. In one embodiment of all aspects the mammalian cell is a Chinese Hamster Ovary (CHO) cell. In one embodiment all aspects the CHO cell is a CHO suspension cell. In one embodiment of all aspects the CHO cell is a CHO-K1 cell.

It has been found that the increase in specific productivity can be achieved over a concentration range of meta-tyrosine added to the culture medium.

In one embodiment of all aspects the meta-tyrosine is added to result at a concentration of from 0.2 mM to 0.7 mM. In one embodiment of all aspects the meta-tyrosine is added to result at a concentration of from 0.25 mM to 0.6 mM. In one embodiment of all aspects the meta-tyrosine is added to result at a concentration of from 0.3 mM to 0.5 mM. In one embodiment of all aspects the meta-tyrosine is added to result at a concentration of from 0.3 mM to 0.4 mM.

In one embodiment of all aspects the specific productivity is increased by at least 5% compared to an identical production process without supplementation of meta-tyrosine. In one embodiment of all aspects the specific productivity is increased by at least 10% compared to an identical production process without supplementation of meta-tyrosine. In one embodiment of all aspects the specific productivity is increased by at least 20% compared to an identical production process without supplementation of meta-tyrosine. In one embodiment of all aspects the specific productivity is increased by at least 25% compared to an identical production process without supplementation of meta-tyrosine.

It has been found that for achieving an increased specific productivity it is not required to perform a temperature-, osmolality- or pH shift and it is also not required to modulate the specific productivity by addition of drugs like valproic acid or sodium butyrate as it is reported in the state of the art. Nevertheless, the person skilled in the art understands that these modifications of the culturing process can also be made/included in the method as reported herein in addition.

In one embodiment of all aspects the use or process is at a constant temperature. In one embodiment of all aspects the use or process is at a temperature which is reduced in the course of the use.

In one embodiment of all aspects the use or process is at a constant pH.

Possible sequence variants (SVs) due to alternative amino acid misincorporation during translation which might occur when meta-tyrosine is added to the culture medium, are controlled by additionally feeding of phenylalanine in non-limiting concentrations.

In Table 1 the amount/frequency/fraction of Phe→xTyr (x means meta-Tyr and/or ortho-Tyr) sequence variant formation for a tracer peptide is shown (maximum level of Phe→xTyr misincorporation by 0.1 mM, 0.3 mM, and 0.4 mM ortho-Tyr and meta-Tyr supplementation at day 14).

From the data of supernatant meta-, ortho-Tyr and L-Phe and respective Phe→xTyr misincorporation of the supplementation experiment the threshold meta-Tyr/Phe and ortho-Tyr/Phe ratios can be calculated which result in final produced sequence fidelity of 99.9%, 99.5%, 99.0%, and 95.0% (referring to ortho- and meta-Tyr misincorporation).

It has been found that a maximal threshold ratio of 1.25, 0.25, 0.125 or 0.025 of meta-Tyr/Phe adjusted in a culture medium can control/avoid unwanted SVs in produced polypeptides (95.0%, 99.0%, 99.5% or 99.9% sequence fidelity, respectively) with at the same time increased specific productivity. This remains increased irrespective of additional Phe supplementation (see FIG. 8).

In one embodiment of all aspects the culture medium additionally comprises phenylalanine in a non-limiting concentration.

In one embodiment of all aspects the molar ratio for meta-tyrosine/phenylalanine is lower than or equal to 1.25. In one embodiment of all aspects the final protein sequence fidelity with respect to Phe→m-Tyr misincorporation is higher than or equal to 95.0%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 95.0%.

In one embodiment of all aspects the molar ratio for meta-tyrosine/phenylalanine is lower than or equal to 0.25. In one embodiment of all aspects the final protein sequence fidelity with respect to Phe→m-Tyr misincorporation is higher than or equal to 99.0%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 99.0%.

In one embodiment of all aspects the molar ratio for meta-tyrosine/phenylalanine is lower than or equal to 0.125. In one embodiment of this aspect the final protein sequence fidelity with respect to Phe→m-Tyr misincorporation is higher than or equal to 99.5%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 99.5%.

In one embodiment of all aspects the molar ratio for meta-tyrosine/phenylalanine is lower than or equal to 0.025. In one embodiment of this aspect the final protein sequence fidelity with respect to Phe→m-Tyr misincorporation is higher than or equal to 99.9%. In one embodiment of this aspect the molar ratio of/for meta-tyrosine/phenylalanine is lower than or equal to 1.25 and the final protein sequence fidelity with respect to Phe→m-Tyr misincorporation is higher than or equal to 99.9%.

DEFINITIONS

"Biomass" as used herein refers to the quantity or weight of cultured cells in the culture medium. Biomass may be measured directly or indirectly by determining viable cell density, total cell density, cell time integral (for viable and total cell density), cell volume time integral (for viable and total cell density), packed cell volume, dry weight or wet weight.

"Bioreactor" as used herein refers to any vessel used for the growth of a mammalian cell culture. Typically a bioreactor will be at least 1 liter and may be 10, 100, 250, 500, 1000, 2500, 5000, 8000, 10,000, 12,000 liters or more, or any volume in between. The internal conditions of the bioreactor, including but not limited to pH, dissolved oxygen and temperature, are typically controlled during the culture period. A bioreactor can be composed of any material that is suitable for holding mammalian cell cultures suspended in media under the culture conditions of the present invention, including glass, plastic or metal.

TABLE 1

| | Sequence Variant | | | |
| --- | --- | --- | --- | --- |
| | Phe → oTyr | | Phe → mTyr | |
| Tracer Peptide | HC66-72 | HC129-140 | HC66-72 | HC129-140 |
| Measured maximum xTyr misincorporation | 1.6-2.0% | 2.3-2.7% | 1.5-2.4% | 1.9-3.0% |
| Calculated penalty factor | 0.5-0.7% | 0.6-0.8% | 1.5-3.0% | 2.0-4.0% |

| | Final Protein Sequence Fidelity | | | |
| --- | --- | --- | --- | --- |
| Surrogate Marker | 99.9% | 99.5% | 99.0% | 95.0% |
| Calculated critical ratios meta-Tyr/Phe | 0.025 | 0.125 | 0.25 | 1.25 |
| Calculated critical ratio ortho-Tyr/Phe | 0.125 | 0.625 | 1.25 | 6.25 |

"Cell density" as used herein refers to the number of cells present in a given volume of medium.

"Cell viability" refers to that portion of cells which are alive at a particular time in relation to the total number of cells, living and dead, in culture at that time.

The term "cell culture," refers to cells growing in suspension or adherent, in roller bottles, flasks, glass or stainless steel cultivations vessels, and the like. Large scale approaches, such as bioreactors, are also encompassed by the term "cell culture". Cell culture procedures for both large and small-scale production of polypeptides are encompassed by the present invention. Procedures including, but not limited to, a fluidized bed bioreactor, shaker flask culture, or stirred tank bioreactor system may be used and operated alternatively in a batch, split-batch, fed-batch, or perfusion mode.

The terms "cell culture medium", "culture medium" or "medium" as used interchangeably within the current invention denote a nutrient solution used for growing mammalian cells. Such a nutrient solution generally includes various factors necessary for growth and maintenance of the cellular environment. For example, a typical nutrient solution may include a basal media formulation, various supplements depending on the cultivation type and, occasionally, selection agents. Typically such solutions provide essential and non-essential amino acids, vitamins, energy sources, lipids and trace elements required by the cell for minimal growth and/or survival. Such a solution may also contain supplementary components that enhance growth and/or survival above the minimal rate including, but not limited to, hormones and/or other growth factors, particular ions, such as sodium, chloride, calcium, magnesium and phosphate, buffer components, vitamins, nucleosides or nucleotides, trace elements, amino acids, lipids and/or glucose or other energy source. A medium is advantageously formulated to a pH and salt concentration optimal for cell survival and proliferation. A medium may be a protein-free medium, i.e. this will contain no full length protein but will contain undefined peptides e.g. from plant hydrolysates. A medium could include human serum albumin and human transferrin but potentially animal-derived insulin and lipids, or a xeno-free medium containing human serum albumin, human transferrin, human insulin and chemically defined lipids. Alternatively, a medium may be a chemically-defined medium, that is a medium wherein all substances are defined and present in defined concentrations. These media could contain only recombinant proteins and/or hormones or a protein-free chemically defined medium, i.e. containing only low molecular weight constituents and synthetic peptides/hormones if required. Chemically defined media could also be completely free of any protein.

The term "cell" or "host cell" refers to a cell into which a nucleic acid, e.g. encoding a heterologous polypeptide, can be or is introduced/transfected. Host cells include both prokaryotic cells, which are used for propagation of vectors/plasmids, and eukaryotic cells, which are used for the expression of the nucleic acid. In one embodiment the eukaryotic cells are mammalian cells. In another embodiment the mammalian host cell is selected from the mammalian cells comprising CHO cells (e.g. CHO-K1 or CHO DG44), BHK cells, NS0 cells, SP2/0 cells, HEK 293 cells, HEK 293 EBNA cells, PER.C6 cells, and COS cells. For the fermentation of the host cell and thus for the expression of the polypeptide of interest a culture medium is used. Generally CHO cells are widely used for the expression of pharmaceutical polypeptides, either at small scale in the laboratory or at large scale in production processes. Due to their wide distribution and use the characteristic properties and the genetic background of CHO cells is well known. Therefore, CHO cells are approved by regulatory authorities for the production of therapeutic proteins for application to human beings. In one embodiment the mammalian cell is a CHO cell. In one embodiment the mammalian cell is a CHO suspension cell line/CHO cell line growing in suspension.

The method according to the current invention is suited for the production of a secreted heterologous polypeptide in large scale, i.e. industrially.

The cultivation of a cell for the production of a desired polypeptide in large scale generally consists of a sequence of individual cultivations, wherein all cultivations except the final, i.e. the large scale, cultivation, i.e. the last one in the sequence, are performed until a certain cell density is reached in the culture vessel. If the predetermined cell density is reached the entire cultivation or a fraction thereof is used to inoculate the next cultivation vessel, which has a larger volume, up to 100 times the volume of the preceding cultivation. All cultivations which serve as a basis for at least one further cultivation in a larger volume are denoted as "seed train fermentation" or "seed train cultivation". Only in the large scale cultivation, i.e. in the cultivation which is not intended to serve as the basis for a further cultivation in a larger volume, which is also denoted as "main fermentation", is the endpoint of the cultivation determined depending on the concentration of the produced secreted heterologous immunoglobulin in the cultivation medium or the cultivation time. The term "large scale" as used within this application denotes the final cultivation of an industrial production process. In one embodiment a large scale cultivation is performed in a volume of at least 100 l, in another embodiment of at least 500 l, in a further embodiment of at least 1000 l up to a volume of 25,000 l. In one embodiment the final, i.e. large scale, cultivation medium does not contain a eukaryotic selection agent.

"Splitting" as used herein is also known as passaging or subculture of cells. This involves transferring a small number of cells into a fresh medium, whereby the split cells seed the new culture. In suspension cultures, a small amount of the culture containing a few cells is diluted into a larger volume of fresh medium.

"Titer" as used herein refers to the total amount of recombinantly expressed polypeptide produced by a mammalian cell culture in a given amount of medium volume. Titer is typically expressed in units of milligrams of polypeptide per milliliter of medium.

A "gene" denotes a nucleic acid which is a segment e.g. on a chromosome or on a plasmid which can effect the expression of a peptide, polypeptide, or protein. Beside the coding region, i.e. the structural gene, a gene comprises other functional elements e.g. a signal sequence, promoter(s), introns, and/or terminators.

A "structural gene" denotes the region of a gene without a signal sequence, i.e. the coding region.

The term "expression" as used herein refers to transcription and/or translation occurring within a cell. The level of transcription of a desired product in a host cell can be determined on the basis of the amount of corresponding mRNA that is present in the cell. For example, mRNA transcribed from a selected nucleic acid can be quantitated by PCR or by Northern hybridization (see Sambrook, et al., Molecular Cloning: A Laboratory Manual, Cold Spring Harbor Laboratory Press (1989)). The protein encoded by a selected nucleic acid can be quantitated by various methods, e.g. by ELISA, by assaying for the biological activity of the protein, or by employing assays that are independent of such activity, such as Western blotting or radioimmunoassay, by using antibodies that recognize and bind to the protein (see Sambrook, et al., 1989, supra).

A "polypeptide" is a polymer of amino acid residues joined by peptide bonds, whether produced naturally or synthetically. Polypeptides of less than about 20 amino acid residues may be referred to as "peptides." Polypeptides comprising two or more amino acid chains or comprising an amino acid chain of a length of 100 amino acids or more may be referred to as "proteins". A polypeptide or protein may also comprise non-peptidic components, such as carbohydrate groups or metal ions. Carbohydrates and other non-peptidic substituents may be added to a protein by the cell in which the protein is produced, and may vary with the type of cell. Proteins and polypeptides are defined herein in terms of their amino acid backbone structure; additions such as carbohydrate groups are generally not specified, but may be present nonetheless. In one embodiment the polypeptide is an immunoglobulin, or an immunoglobulin-fragment, or an immunoglobulin-conjugate. In one embodiment the polypeptide is an immunoglobulin heavy chain or an immunoglobulin light chain or a fragment, fusion or conjugate thereof. An "exogenous" or "non-endogenous" polypeptide is a polypeptide that does not originate from within the used host cell.

The term "nucleic acid" as used herein, is a polymer consisting of individual nucleotides, i.e. a polynucleotide. It refers to a naturally occurring, or partially or fully non-naturally occurring nucleic acid, which is e.g. encoding a polypeptide that can be produced recombinantly. The nucleic acid can be build up of DNA-fragments which are either isolated or synthesized by chemical means. The nucleic acid can be integrated into another nucleic acid, e.g. in an expression plasmid or the genome/chromosome of a host cell. Plasmid includes shuttle and expression vectors. Typically, the plasmid will also comprise a prokaryotic propagation unit comprising an origin of replication (e.g. the ColE1 origin of replication) and a selectable marker (e.g. ampicillin or tetracycline resistance gene) for replication and selection, respectively, of the vector in bacteria.

The term "immunoglobulin" denotes a molecule comprising at least two so called light chain polypeptides (light chain) and two so called heavy chain polypeptides (heavy chain). Each of the heavy and light chain polypeptides comprises a variable domain (variable region) (generally the amino terminal portion of the polypeptide chain) comprising binding regions that are able to interact with an antigen. Each of the heavy and light chain polypeptides also comprises a constant region (generally the carboxy-terminal portion). The constant region of the heavy chain mediates the binding of the immunoglobulin i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component C1q.

The term "immunoglobulin" herein is used in the broadest sense and encompasses various immunoglobulin structures, including but not limited to monoclonal antibodies, polyclonal antibodies, multispecific antibodies (e.g., bispecific antibodies), and immunoglobulin fragments so long as they exhibit the desired antigen-binding activity.

Depending on the amino acid sequence of the constant region of the heavy chains, immunoglobulins are divided in different classes: IgA class, IgD class, IgE class, IgG class, and IgM class. Some of these classes are further divided into subclasses (isotypes), i.e. IgG in IgG1, IgG2, IgG3, and IgG4, or IgA in IgA1 and IgA2. According to the class to which an immunoglobulin belongs the heavy chain constant regions are called α (IgA), δ (IgD), ε (IgE), γ (IgG), and μ (IgM), respectively. In one embodiment the immunoglobulin is an immunoglobulin of the IgG class. In another embodiment the immunoglobulin has a human constant region or a constant region derived from human origin. In a further embodiment the immunoglobulin is of the IgG4 subclass or the IgG1, IgG2, or IgG3 subclass, which is modified in such a way that no Fcγ receptor (e.g. FcγRIIIa) binding and/or no C1q binding can be detected. In one embodiment the immunoglobulin is of the human IgG4 subclass or a mutated human IgG1 subclass. In one embodiment the immunoglobulin is of the human IgG1 subclass with mutations L234A and L235A. In another embodiment the immunoglobulin is in regard to Fcγ receptor binding of IgG4 subclass or of IgG1 or IgG2 subclass, with a mutation in L234, L235, and/or D265, and/or contains the PVA236 mutation. In a further embodiment the immunoglobulin has a mutation selected from S228P, L234A, L235A, L235E, SPLE (S228P and L235E), and/or PVA236 (PVA236 means that the amino acid sequence ELLG (given in one letter amino acid code) from amino acid position 233 to 236 of IgG1 or EFLG of IgG4 is replaced by PVA). In one embodiment the immunoglobulin is of the IgG4 subclass and has the mutation S228P of IgG4, or the immunoglobulin is of the IgG1 subclass and has the mutations L234A and L235A.

The variable domain of an immunoglobulin's light or heavy chain in turn comprises different segments, i.e. four framework regions (FR) and three hypervariable regions (CDR).

An "immunoglobulin fragment" denotes a polypeptide comprising at least one domain of the group of domains comprising the variable domain, the $C_H1$ domain, the hinge-region, the $C_H2$ domain, the $C_H3$ domain, the $C_H4$ domain of a heavy chain of an immunoglobulin or the variable domain or the $C_L$ domain of a light chain of an immunoglobulin. Also comprised are derivatives and variants thereof. Additionally a variable domain, in which one or more amino acids or amino acid regions are deleted, may be present.

An "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, growth receptor, anti-fusogenic peptide or the like.

As used herein "Phe non-limiting" or "Phe non-limitation" concentration means that phenylalanine is fed in excessive amounts, i.e. that there is a supplementation of the culture with e.g. 0.6 mM Phe per day starting at day 6 until day 14. Without additional feeding, Phe will in general be limiting by day 10 or 11 ("Phe limitation"). Phenylalanine supplementation can be added by continuous feeding or alternatively by one or more individual bolus shots of Phe stock solutions at the beginning or during the fermentation process.

The term "increased specific productivity" means that the specific productivity of a respective host cell is higher under conditions described herein, relative to an identical production process without supplementation of meta-tyrosine. The specific productivity (qP) as a measure for the production capacity (amount of polypeptide/protein produced, e.g. in picogram) of a cell per day is calculated as reflected in the examples.

DESCRIPTION OF THE FIGURES

Meta-Tyr modulates CHO biomass generation under Phe limitation conditions. (FIG. 1A) For the fed-batch process two serial continuous feeds, feed 1 and feed 2, were used. CHO fed-batch cultivations were supplemented with either non (control), 0.1 mM, 0.3 mM, or 0.4 mM para-Tyr, ortho-Tyr, or meta-Tyr in the beginning of the process. The cell time integral (CTI), as measure of CHO cell biomass generation, is shown for para-Tyr (FIG. 1B), ortho-Tyr (FIG. 1C) and meta-Tyr (FIG. 1D) supplementation.

Figure 1A:
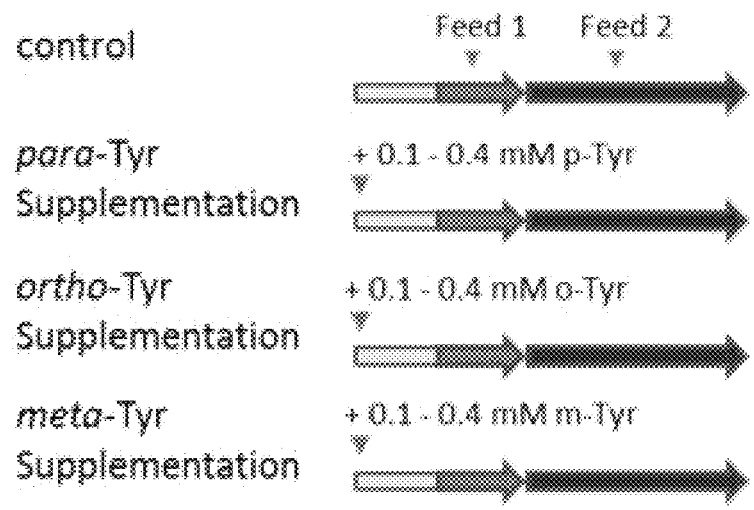
FIGS. 1A, 1B, 1C, and 1D
Figure 1B:
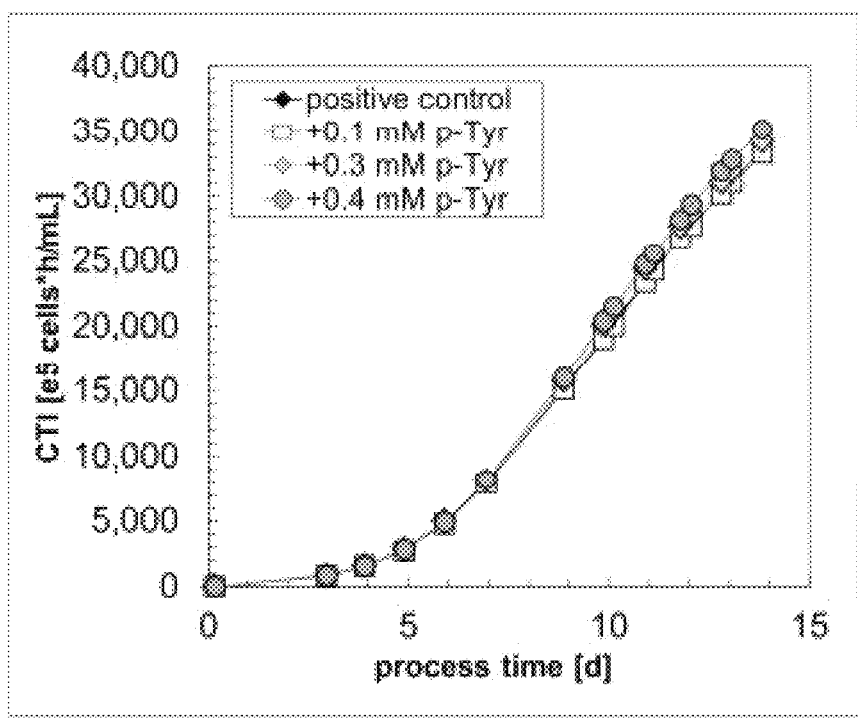
Figure 1C:
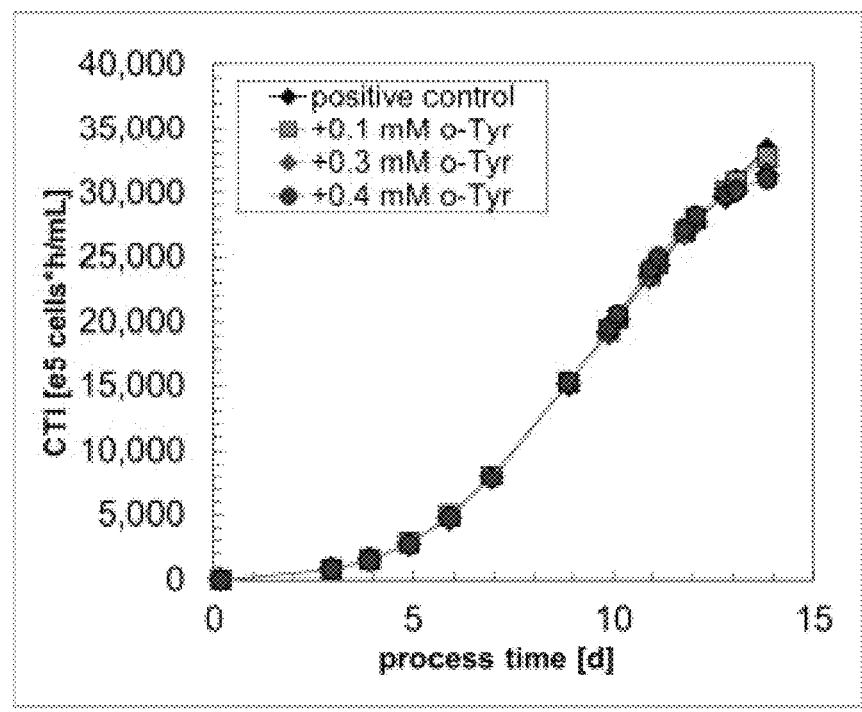
Figure 1D:
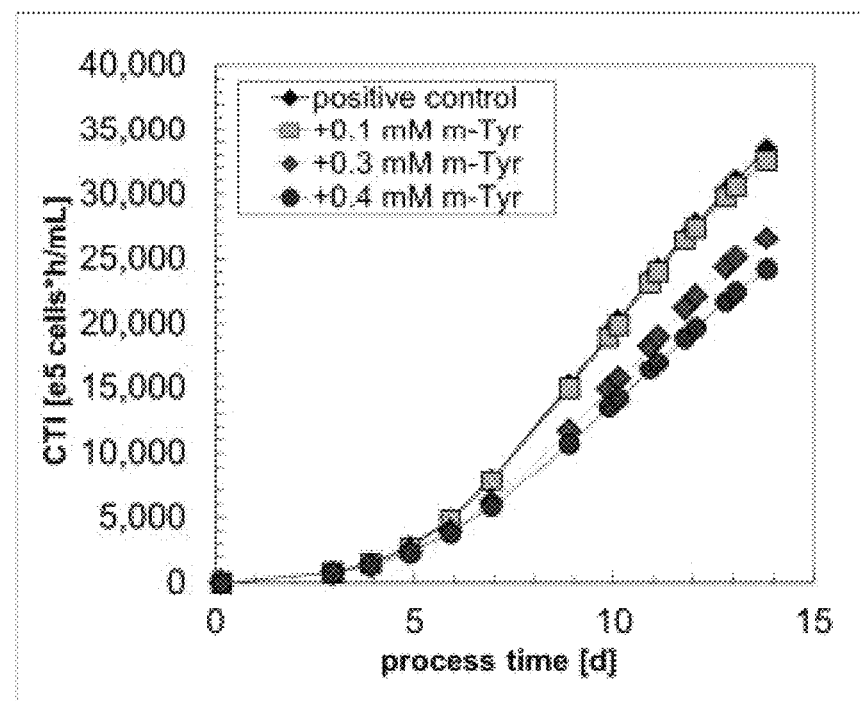
Figure 2A:
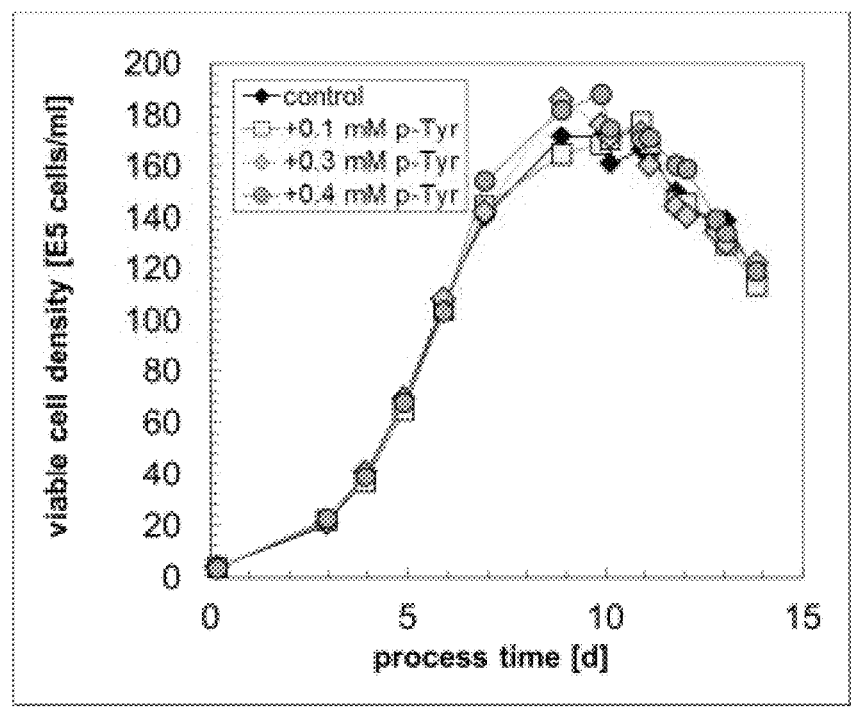
FIGS. 2A, 2B, and 2C
Figure 2B:
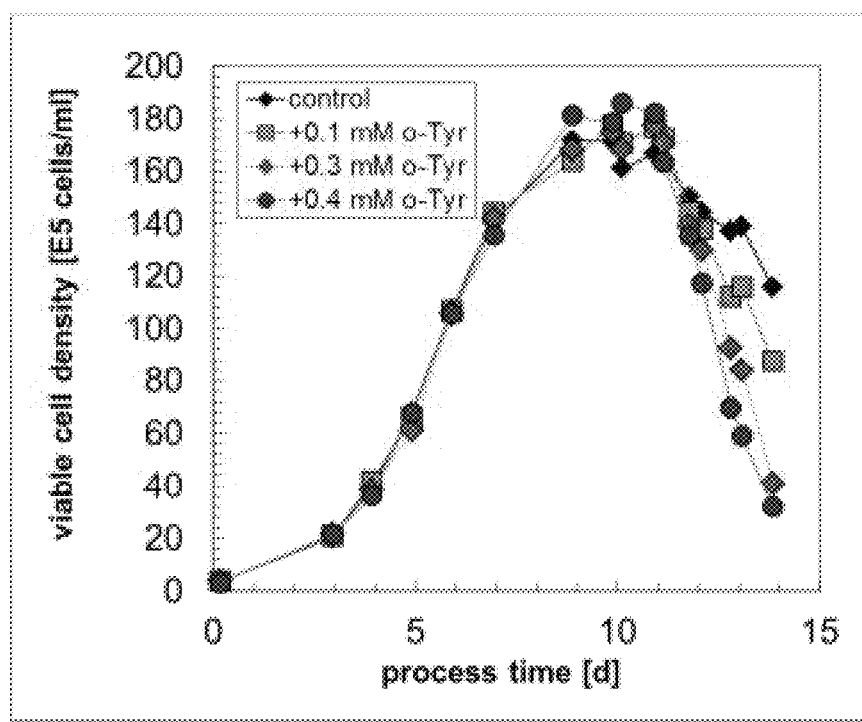
Figure 2C:
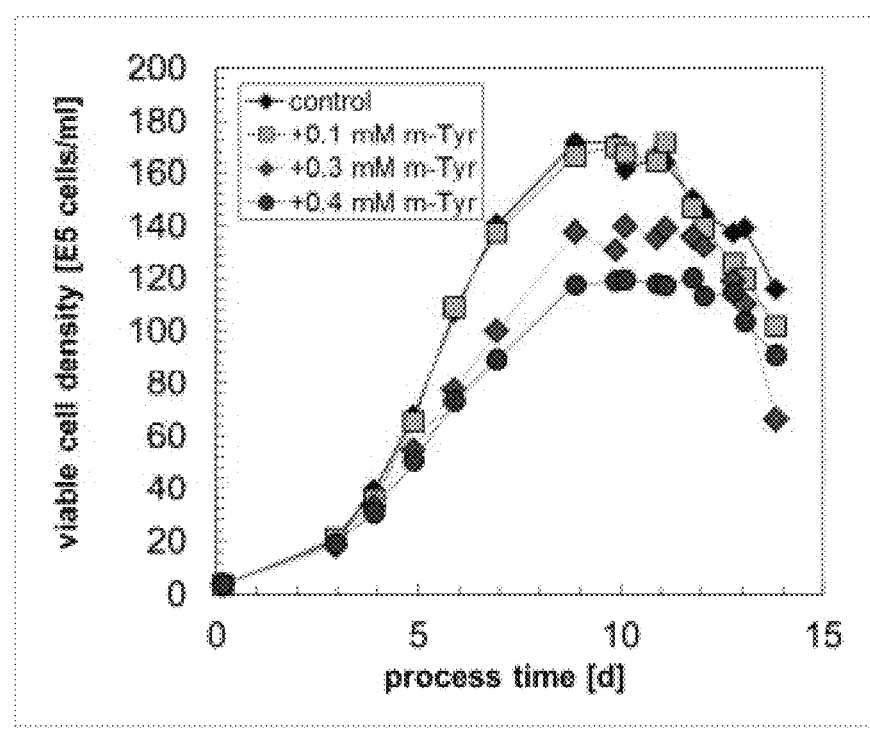

Different roles of meta-Tyr and ortho-Tyr in CHO cell growth regulation under Phe limitation conditions. The viable cell density is shown for para-Tyr (FIG. 2A), ortho-Tyr (FIG. 2B) and meta-Tyr (FIG. 2C) supplementation. Fed-batch cultivation with no para-Tyr, ortho-Tyr or meta-Tyr supplementation is shown as control.

Figure 3A:
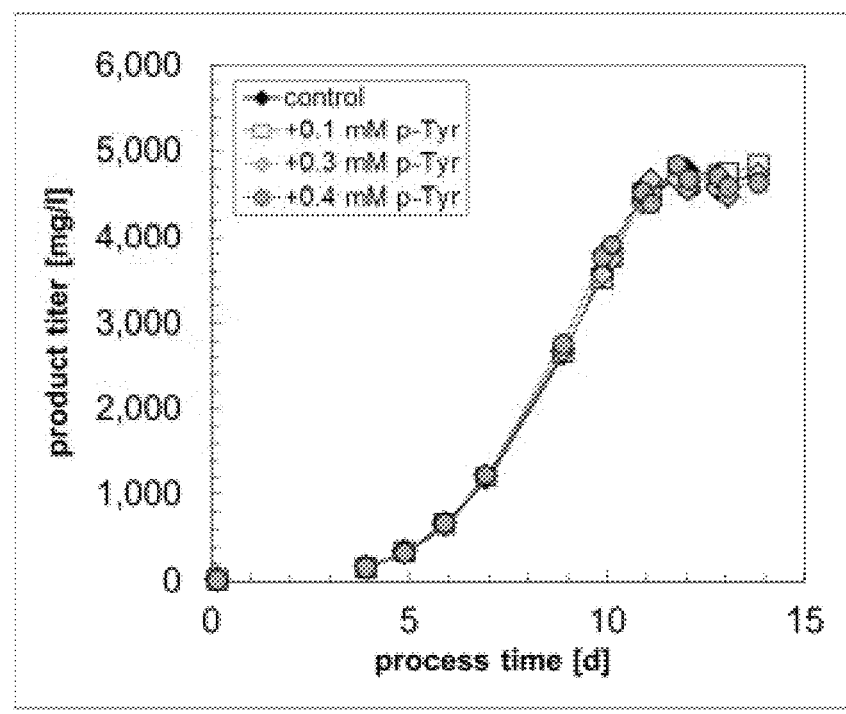
Figure 3B:
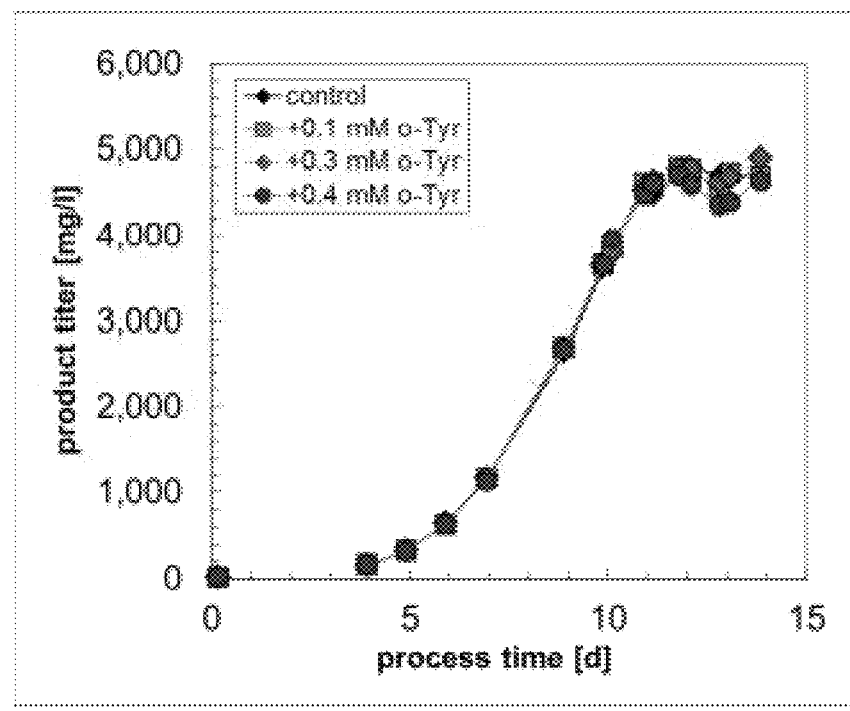
Figure 3C:
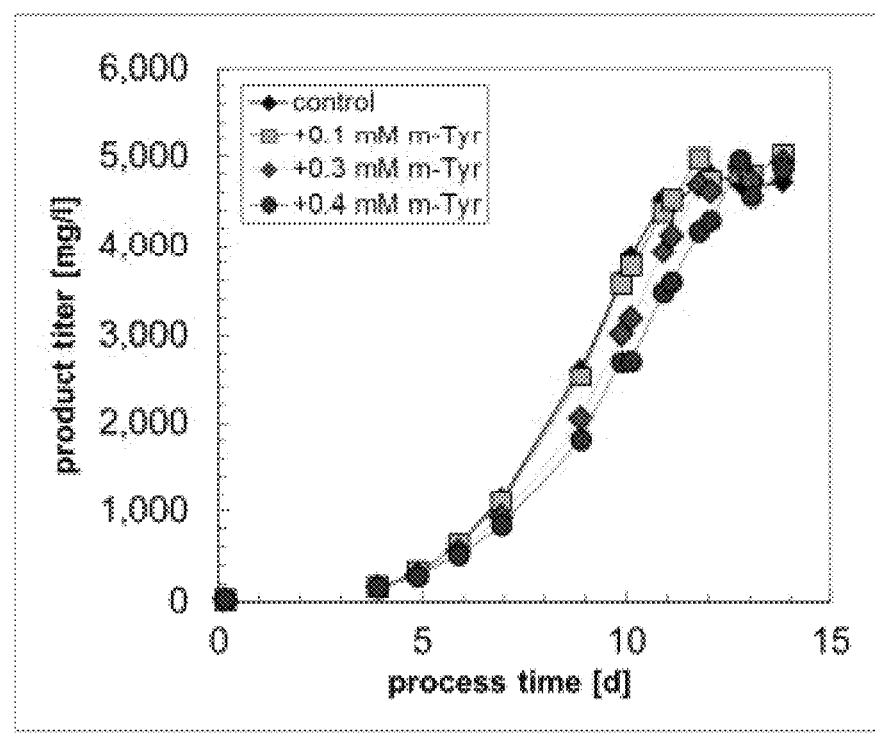

FIGS. 3A, 3B, and 3C

Supplementation of meta-Tyr and ortho-Tyr in CHO fed-batch cultivations does not alter product yield under Phe limitation conditions. The product concentration is shown for para-Tyr (FIG. 3A), ortho-Tyr (FIG. 3B) and meta-Tyr (FIG. 3C) supplementation. Fed-batch cultivation with no para-Tyr, ortho-Tyr or meta-Tyr supplementation is shown as control.

Figure 4A:
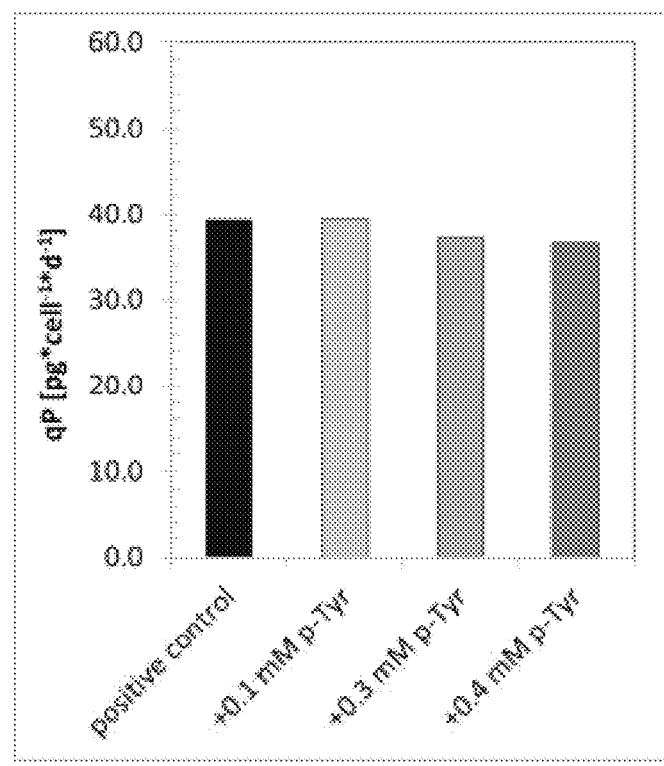
Figure 4B:
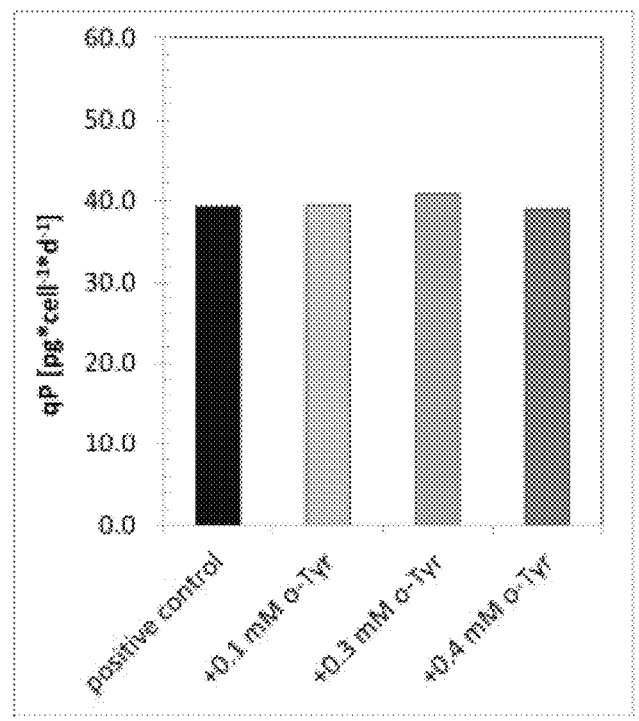
Figure 4C:
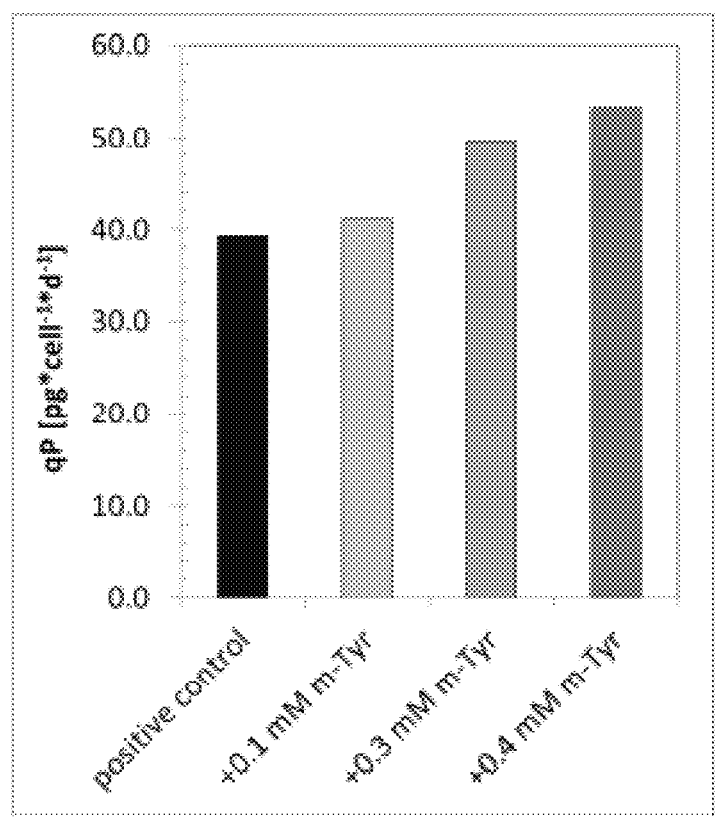
Figure 5A:
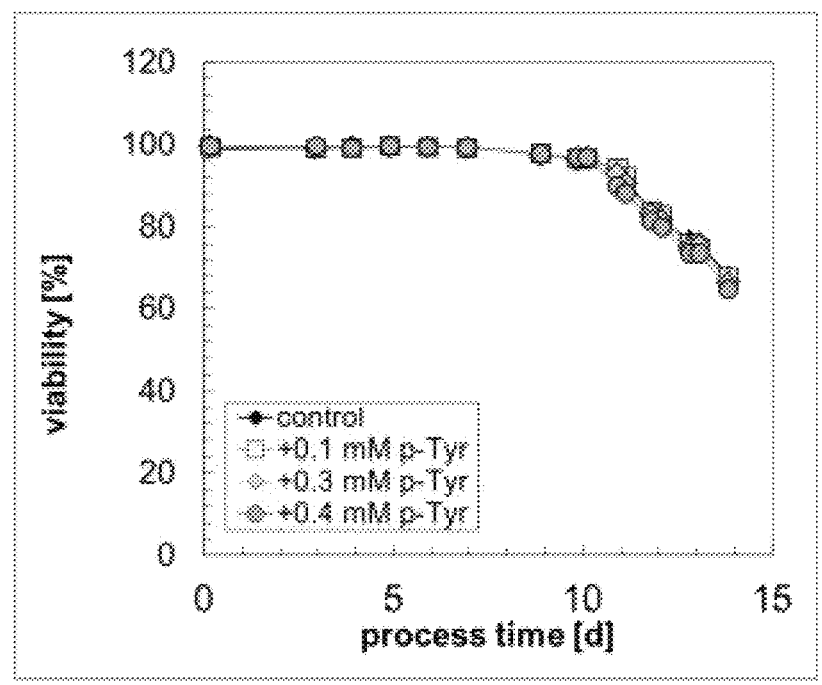
Figure 5B:
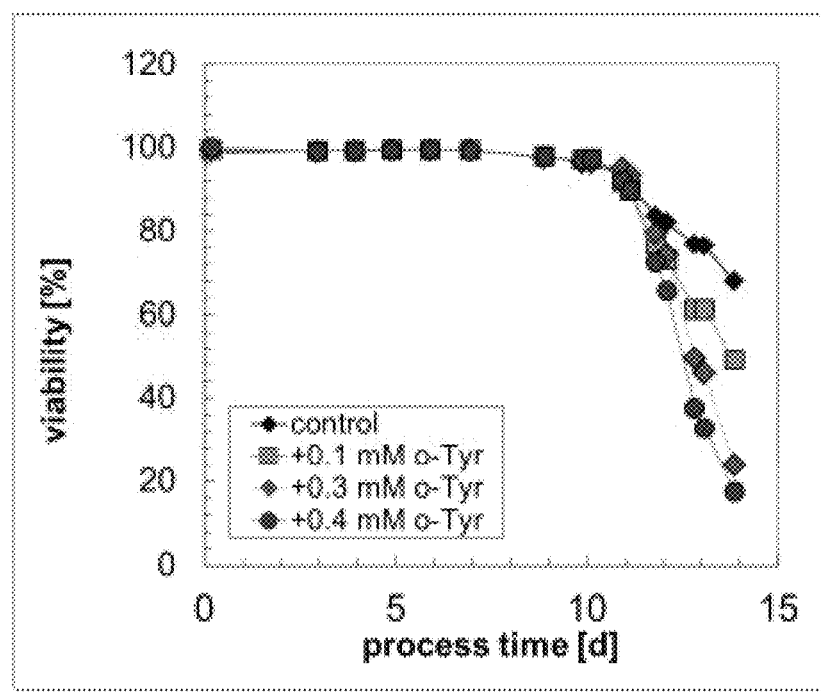
Figure 5C:
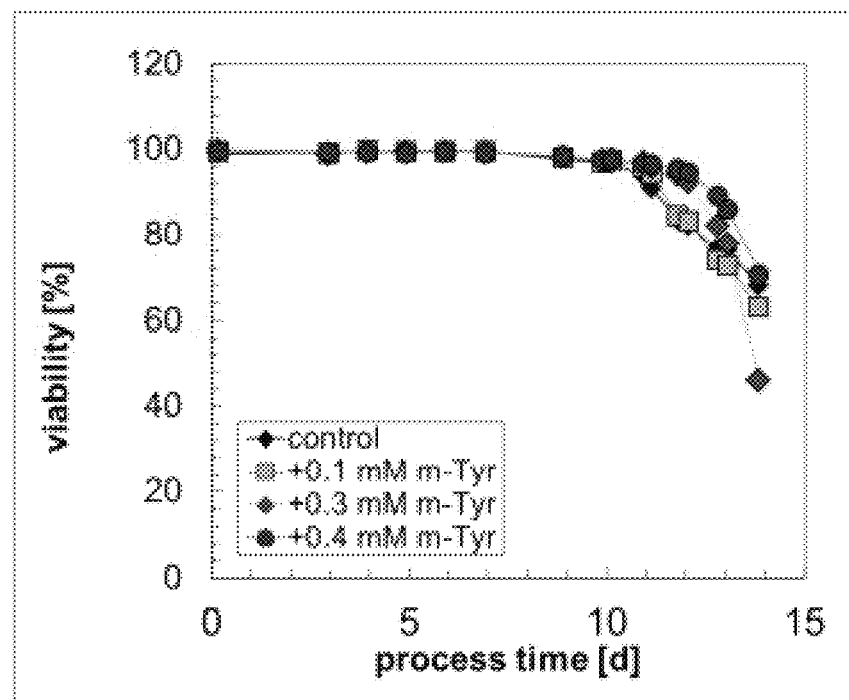
Figure 5D:
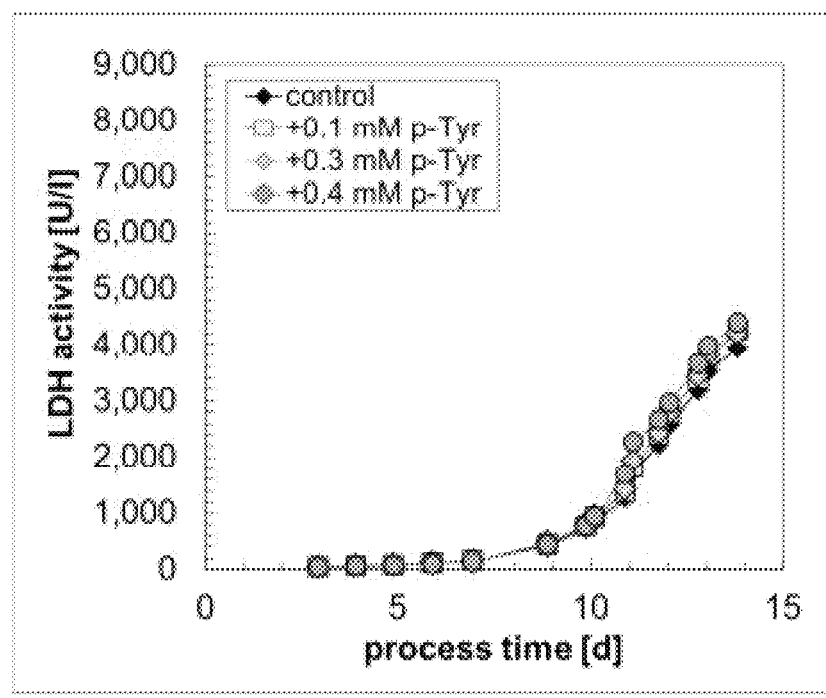
Figure 5E:
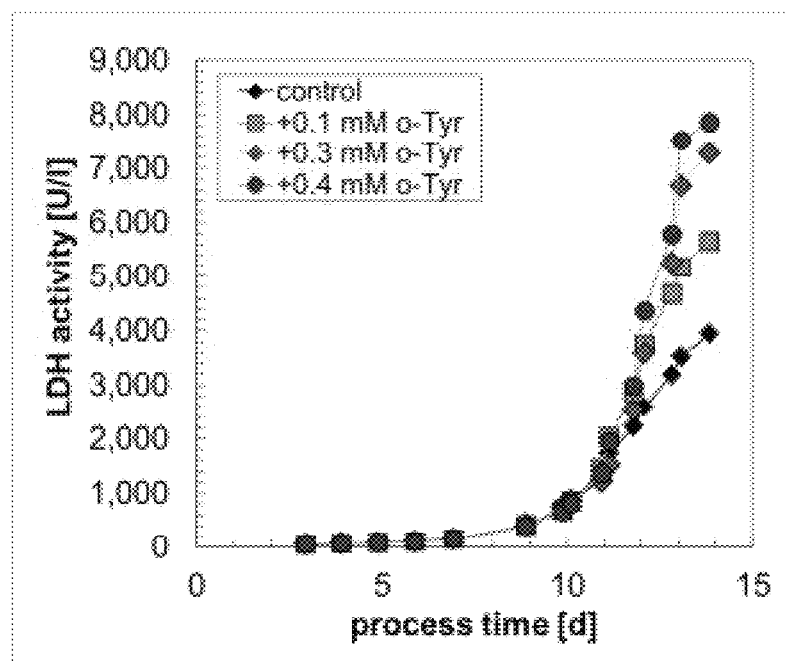
Figure 5F:
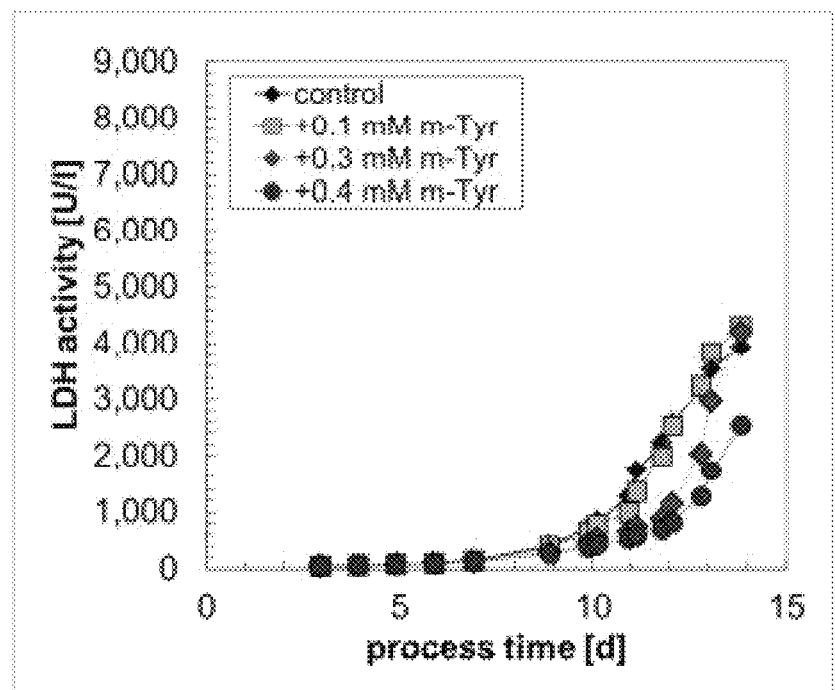
Figure 6A:
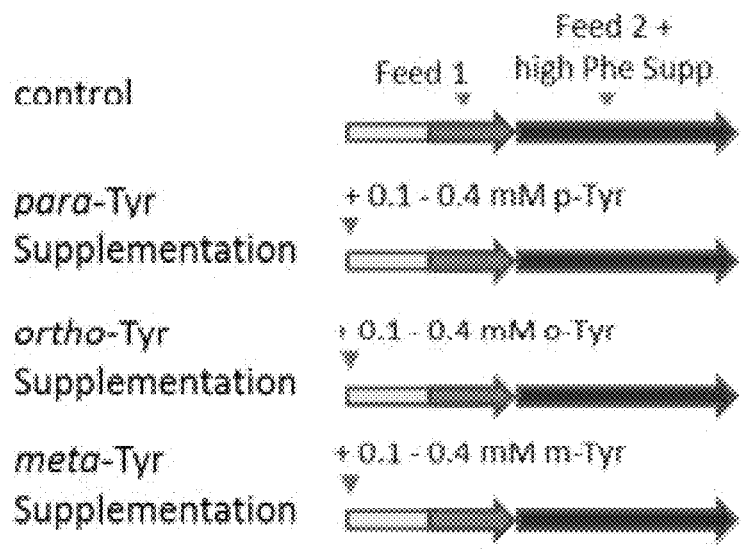
Figure 6B:
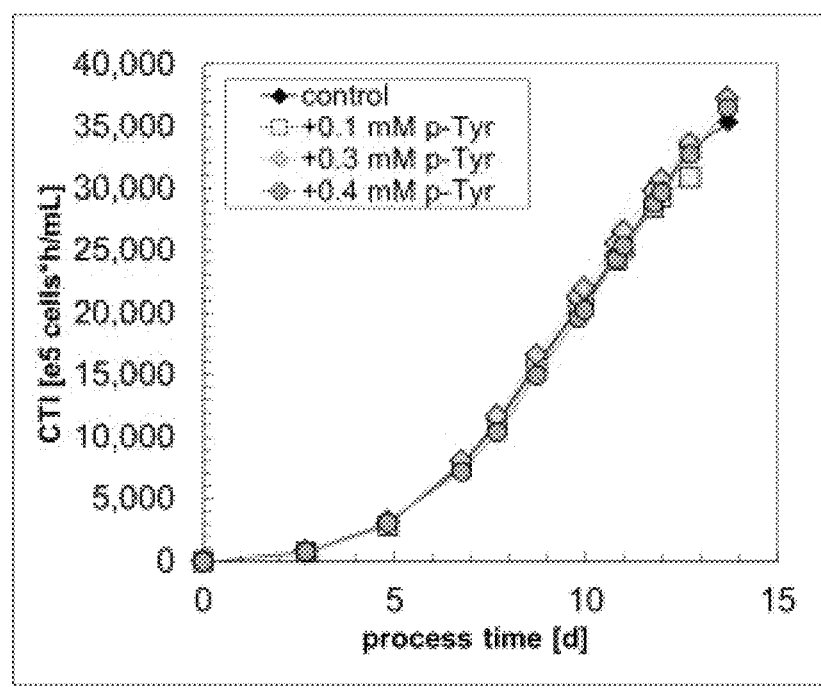
Figure 6C:
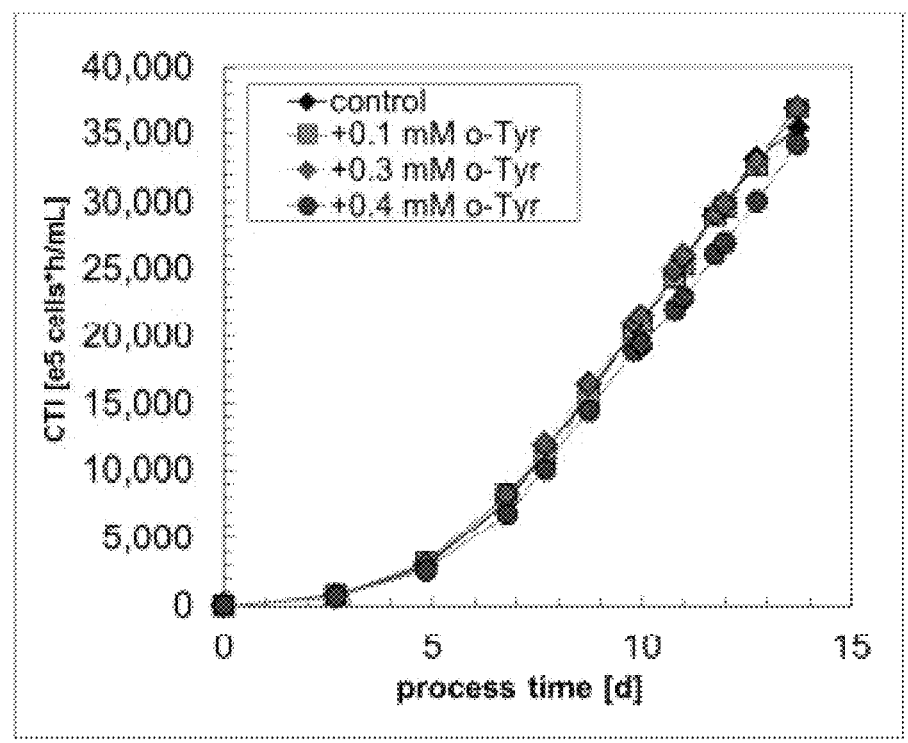
Figure 6D:
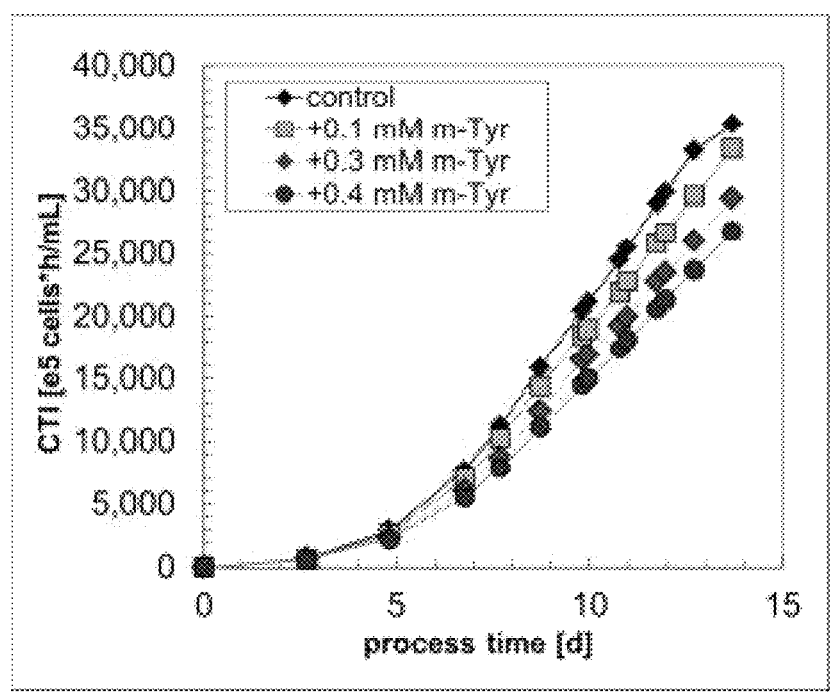

FIGS. 4A, 4B, and 4C

Meta-Tyr supplementation increases cell-specific product formation rate qP under Phe limitation conditions. The cell-specific product formation rate qP is shown for para-Tyr (FIG. 4A), ortho-Tyr (FIG. 4B) and meta-Tyr (FIG. 4C) supplementation. Fed-batch cultivation with no para-Tyr, ortho-Tyr or meta-Tyr supplementation is shown as control.

FIGS. 5A, 5B, 5C, 5D, 5E, and 5F

Different roles of meta-Tyr and ortho-Tyr for CHO cell viability under Phe limitation conditions. The cell viability and supernatant LDH activity are shown for para-Tyr (FIG. 5A, FIG. 5D), ortho-Tyr (FIG. 5B, FIG. 5E) and meta-Tyr (FIG. 5C, FIG. 5F) supplementation. Fed-batch cultivation with no para-Tyr, ortho-Tyr or meta-Tyr supplementation is shown as control.

FIGS. 6a, 6B, 6C, and 6D

Meta-Tyr modulates CHO biomass generation under Phe non-limitation conditions. (FIG. 6A) For the fed-batch process two serial continuous feeds, feed 1 and feed 2 with high Phe concentration, were used. CHO fed-batch cultivations were supplemented with either non (control), 0.1 mM, 0.3 mM, or 0.4 mM para-Tyr, ortho-Tyr, or meta-Tyr in the beginning of the process. The cell time integral (CTI), as measure of CHO cell biomass generation, is shown for para-Tyr (FIG. 6B), ortho-Tyr (FIG. 6C) and meta-Tyr (FIG. 6D) supplementation.

Figure 7A:
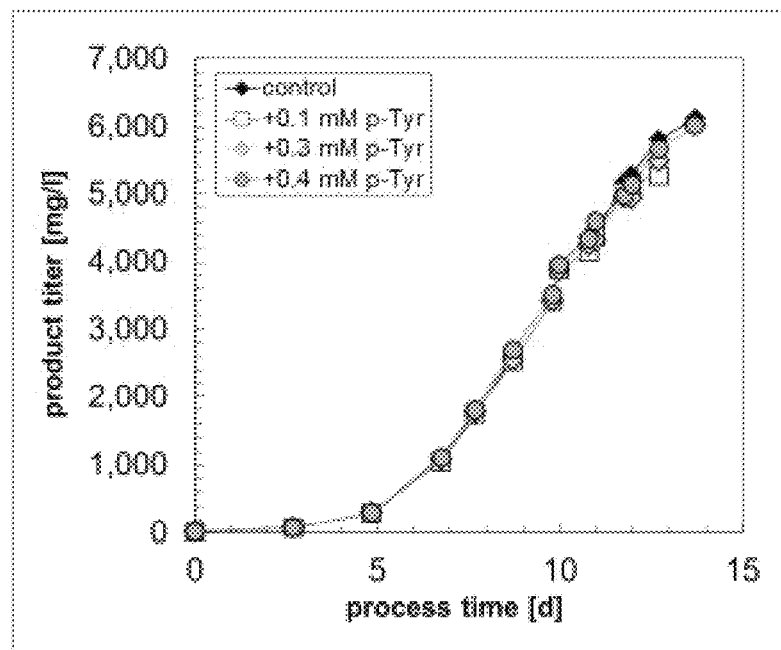
Figure 7B:
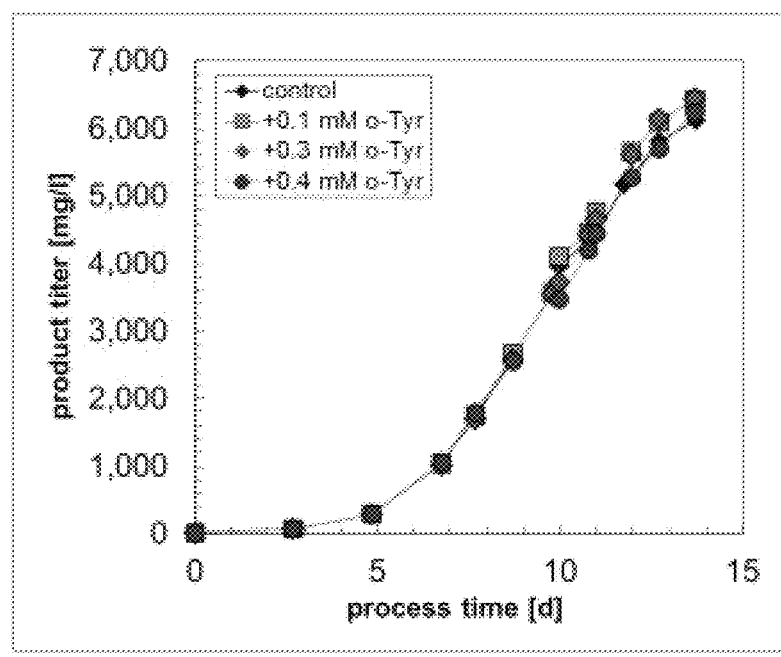
Figure 7C:
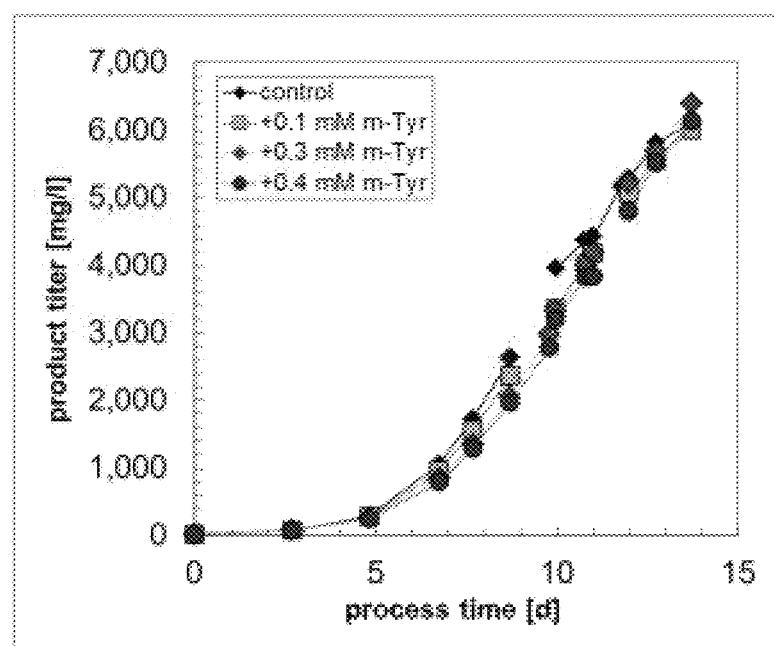

FIGS. 7A, 7B, and 7C

Supplementation of meta-Tyr and ortho-Tyr in CHO fed-batch cultivations does not alter product yield under Phe non-limitation conditions. The product concentration is shown for para-Tyr (FIG. 7A), ortho-Tyr (FIG. 7B) and meta-Tyr (FIG. 7C) supplementation. Fed-batch cultivation with no para-Tyr, ortho-Tyr or meta-Tyr supplementation is shown as control.

Figure 8A:
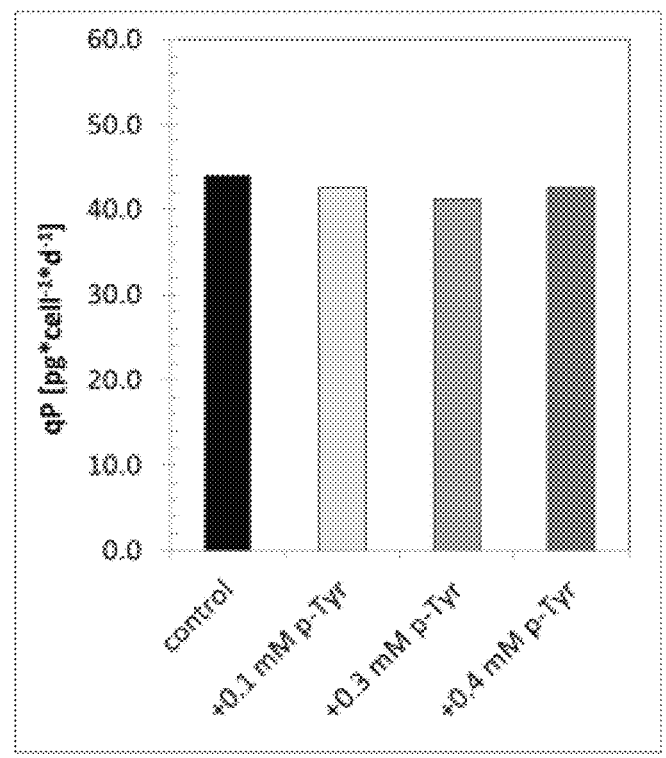
Figure 8B:
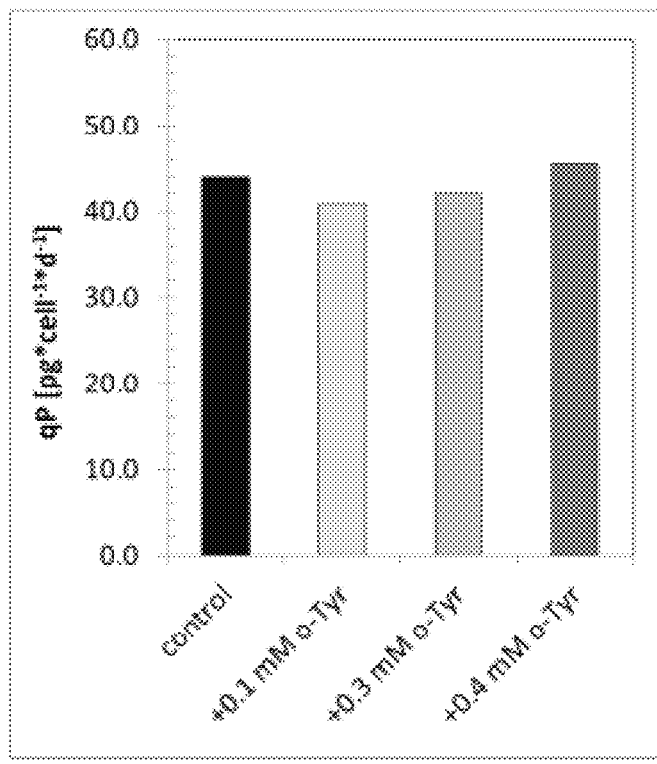
Figure 8C:
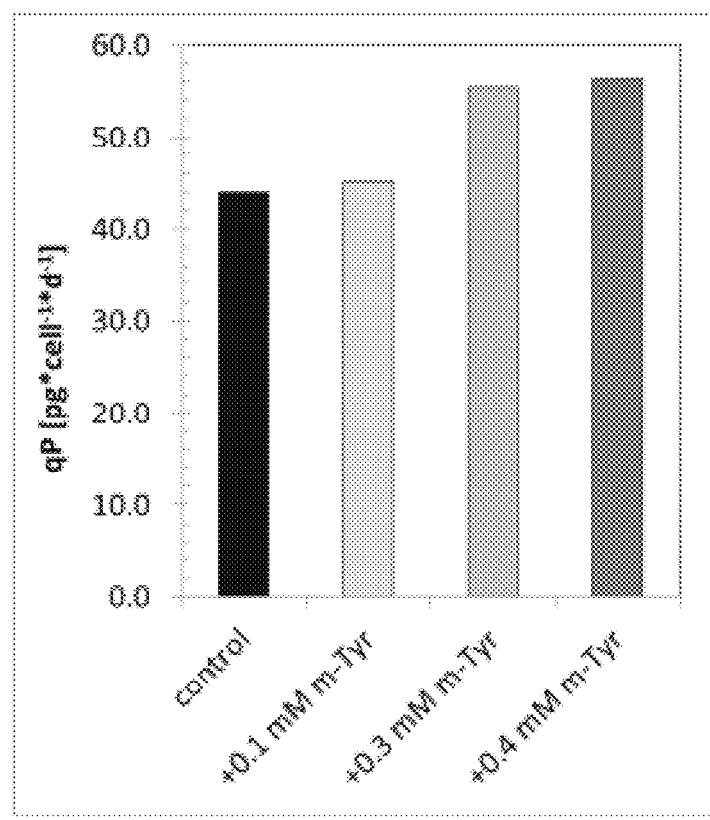

FIGS. 8A, 8B, and 8C

Meta-Tyr supplementation increases cell-specific product formation rate qP under Phe non-limitation conditions. The cell-specific product formation rate qP is shown for para-Tyr (FIG. 8A), ortho-Tyr (FIG. 8B) and meta-Tyr (FIG. 8C) supplementation. Fed-batch cultivation with no para-Tyr, ortho-Tyr or meta-Tyr supplementation is shown as control.

EXAMPLES

The following examples and figures are provided to aid the understanding of the present invention, the true scope of which is set forth in the appended claims. It is understood that modifications can be made in the procedures set forth without departing from the spirit of the invention.

Reagents and Material

DL-ortho-tyrosine (2-hydroxy-DL-phenylalanine), DL-meta-tyrosine (3-hydroxy-DL-phenylalanine), L-para-tyrosine, L-phenylalanine, and guanidinium hydrochloride were obtained from Sigma-Aldrich (Munich, Germany). L-ortho-tyrosine (2-hydroxy-L-phenylalanine) and L-meta-tyrosine (3-hydroxy-L-phenylalanine) were purchased from RSP Amino Acids, LLC (Shirley, Mass., USA). All other reagents were purchased from Merck (Darmstadt, Germany) and Sigma-Aldrich (Munich, Germany).

Cells and Cell Cultivation

For all cell culture experiments a recombinant CHO-K1 cell line, called clone 1, expressing a humanized monoclonal antibody was used. The recombinant CHO-K1 cell line was generated using an L-methionine sulfoximine sensitive CHO-K1 host cell line (Lonza, Cologne, Germany). The cells were cultivated in protein free, chemically defined CD-CHO medium (Life Technologies, Darmstadt, Germany) supplemented with 50 M L-methionine sulfoximine (Sigma Aldrich, Munich, Germany) during seed train cultivation. Seed train cultivation was performed in shake flasks using a humidified incubator, 7% $CO_2$, and 37° C. setting. The cells were splitted every three to four days for subcultivation and culture expansion. For all experiments, cells with identical age in culture (appr. 21 generations) until start of the experiment were used.

Meta-Tyr and Ortho-Tyr Supplementation Experiments

All supplementation experiments were performed using shake flask cultivation systems, chemically defined CD-CHO medium without the selection pressure L-methionine sulfoximine and two appropriate serial continuous applied feeds (feed 1 and feed 2). Recombinant CHO-K1 cells producing a humanized monoclonal antibody were inoculated with $3 \times 10^5$ viable cells/mL and cultured for 14 days. CD-CHO base medium was sterile supplemented before inoculation with 0.1 mM, 0.3 mM or 0.4 mM of either ortho-Tyr, meta-Tyr or para-Tyr. Control cultivation with no supplementation of ortho-Tyr, meta-Tyr or para-Tyr was used as reference. Phenylalanine (Phe) non-limitation conditions were realized by increasing concentration of Phe in feed 2.

Viable Cell Densities, Viability and Cell Time Integral

For analysis of viable and total cell densities an automated Cedex HiRes system (Roche Diagnostics, Mannheim, Germany) was used. Discrimination of viable and total cell densities were evaluated using the trypan blue exclusion staining method and analyzing more than 10 pictures per sample and day according to the manufacturer's specifications. Viable cell density (VCD) and cell viability were calculated as described in equation 1 (Equ 1) and equation 2 (Equ 2), respectively.

$$\text{Viable cell density} = N_{Trypan\ blue\ negative} \times (10^5 \text{ viable cells/ml}) \quad \text{(Equ 1)}$$

$$\text{Cell viability} = N_{Trypan\ blue\ negative} / (N_{Trypan\ blue\ negative} + N_{Trypan\ blue\ positive}\ \text{cells}) \times 100\% \quad \text{(Equ 2)}$$

As indicator for overall biomass generation in the process a cumulative cell time integral (CTI) was calculated as followed (Equ 3).

$$\text{Cell time integral} = \Sigma(0.5 \times (VCD_{n-1} + VCD_n) \times (t_n - t_{n-1})) \times (10^5 \text{ viable cells} \times d/ml) \quad \text{(Equ 3)}$$

Lactate dehydrogenase (LDH) activity in the cell-free supernatant was analyzed using a Cobas Integra 400 plus system (Roche Diagnostics, Mannheim, Germany).

Quantification of IgG Titer and Calculation of qP

Product titer war either quantified by a Cobas Integra 400 plus system (Roche, Mannheim, Germany) according to the manufacture's protocol or by PorosA HPLC method as described previously (Zeck et al. 2012). The overall specific productivity qP was calculated for the analysis of cell production capacity according to equation 4.

$$qP = (\text{Titer}_n - \text{Titer}_{n-1})/(CTI_n - CTI_{n-1}) \times (\text{pg}/(\text{viable cell} \times d)) \quad \text{(Equ 4)}$$

Determination of Peptide Sequence Variants and Identification of Meta- and Ortho-Tyr Sequence Variants with Synthetic Peptides Quantification of peptide sequence variants were performed as described previously (Zeck et al. 2012). Briefly, antibody samples (250 µg) were denatured by addition of denaturing buffer (0.4 M Tris, 8 M guanidinium hydrochloride, pH 8) to a final volume of 240 µL. Reduction was achieved by addition of 20 µL of 0.24 M DTT freshly prepared in denaturing buffer and incubation at 37° C. for 60 min. Subsequently, the sample was alkylated by addition of 20 µL of 0.6 M iodoacetic acid in water for 15 min at room temperature in the dark. The excess of alkylation reagent was inactivated by addition of 30 µL of DTT solution. The sample was than buffer exchanged to approximately 480 µL of 50 mM Tris/HCl, pH 7.5 using NAP 5 Sephadex G-25 DNA grade columns (GE Healthcare, Munich, Germany). Digestion was performed with trypsin for 5 h at 37° C. (ratio 1:37). The peptide mixture obtained was injected and separated without pretreatment using reversed phase HPLC (Agilent 1100 Cap LC, Agilent Technologies, Böblingen, Germany). A Polaris 3 C18-ether column (1×250 mm; 3 µm particle diameter, 180 Å pore size) from Varian (Darmstadt, Germany) was used for separation. The solvents were 0.1% formic acid in water (A) and in acetonitrile (B) (Sigma Aldrich, Munich, Germany). A linear gradient from 2 to 38% B was run over 80 min at 37° C. The HPLC eluate was split using Triversa NanoMate (Advion, Ithaca, N.Y.) and 380 nL/min were infused into a LTQ Orbitrap classic tandem mass spectrometer (Thermo Fisher Scientific, Dreieich, Germany) operating in positive ion mode. For confirmation of ortho- and meta-Tyr peaks in extracted ion chromatograms we used synthetic peptides of mAb HC66-72 DQFTISR (unmodified), DQpYTISR, DQmYTISR, and DQoYTISR. Synthetic peptides were purchased from Biosyntan GmbH (Berlin, Germany).

Calculation of Penalty Factors and Surrogate Makers for Phe-Ortho-Tyr and Phe-Meta-Tyr Sequence Variant Prediction We hypothesize that the incorporation of meta- and/or ortho-Tyr instead of Phe can be described by a simplified model which assumes that the use of meta- and/or ortho-Tyr instead of Phe is penalized. This penalty factor can result from different sources such as a better transport of L-Phe into the cells and/or an editing mechanism during protein synthesis which tries to prevent the use of meta- and/or ortho-Tyr. This assumption leads to the equation $$p \times r \times [x] = [y], \quad \text{(Equ 5)}$$

where p is the penalty factor, r is the ratio of average meta- or ortho-Tyr vs. Phe concentrations (during a given time interval), [x] is the concentration of protein produced (in the time interval) and [y] is the concentration of protein produced which has the sequence variant. Note that this model does not include any dependencies on time, process stage, Phe and meta- or ortho-Tyr concentration ratios that lead to, e.g. phase shifts. The calculation of the penalty factor is straightforward (Equ 7).

$$p = [y]/(r \times [x]) \quad \text{(Equ 6)}$$

Similarly, knowing the penalty factor it is also possible to calculate ratios of meta- or ortho-Tyr to Phe concentrations for a desired percentage of product without sequence variants.

Example 1

Effects of Meta-Tyrosine Supplementation on Modulation of Specific Productivity (qP) Under Phenylalanine Limitation Conditions Previously, Gurer-Orhan et al. reported that meta-Tyr supplementation of CHO cells showed dose-dependent cell cytotoxicity. In concentration screens, a 50% reduction of the MTX reduction capacity of CHO cells was observed when supplemented with 0.5 mM meta-Tyr (Gurer-Orhan et al., (2006)). No data or concentration have been reported for ortho-Tyr supplementation in cell cultures to date. Using a dose-dependent cultivation approach, it was aimed to determine the relevance and tolerable concentrations of meta-Tyr and ortho-Tyr on CHO cell growth performance. For this, a CHO cultivation model described in material and methods was supplemented with either 0.1 mM, 0.3 mM or 0.4 mM para-Tyr, ortho-Tyr or meta-Tyr. We used the standard cultivation process with no supplementation as reference, following so-called "control" or "positive control". Here, Phe will go into limitation by day 10/11.

In a first approach, the role of meta- and ortho-Tyr on the macroscopic cell growth markers, viable cell density (VCD), cell viability and cell time integral (CTI) as marker for overall biomass production was analyzed. On day 9/10, all cultures tested, except the one with meta-Tyr supplementation, reached a maximum VCD of approximately 180×10⁵ cells/ml, while CHO clone 1 treated with meta-Tyr showed dose dependent reduced maximal VCD (FIG. 2). A decreased cumulative CTI for the meta-Tyr supplemented CHO cultures was observed (FIG. 1).

In contrast to data published by Gurer-Orhan et al. previously, no significant impact of meta-Tyr supplementation on cell viability in our fed-batch CHO cultivation model was observed. However, supplementation of ortho-Tyr showed lower cell viability with less than 60% on day 14 and higher final LDH activity in the supernatant compared to control and meta-Tyr, as well para-Tyr supplementation (FIG. 5).

The overall productivity of the cultures, determined by product concentration analysis, revealed no differences between the test cases (FIG. 3). All cultures showed titer stagnation from day 11/12 on. Additionally, meta-Tyr alone showed an overall higher specific productivity qP (FIG. 4). Supplementation of 0.1 mM, 0.3 mM, and 0.4 mM meta-Tyr under Phe limitation conditions increased qP compared to control by +5%, +26%, and +36%, respectively.

Example 2

Effects of Meta-Tyrosine Supplementation on Modulation of Specific Productivity (qP) Under Phenylalanine Non-Limitation Conditions In a second approach, the role of meta- and ortho-Tyr supplementation under Phe non-limitation conditions in CHO fed-batch cultivations was analyzed. For that, the amount of Phe in feed 2 was increased to prevent Phe limitation (FIG. 6).

Again, all cultures tested, except the one with meta-Tyr supplementation, reached similar CTIs of approximately 35,000 to 40,000×10⁵ cells*h/ml, while CHO clone 1 treated with meta-Tyr showed dose dependent reduction in CTI (FIG. 6). No differences were observed in product titer for all tested conditions (FIG. 7). However, compared to Phe limitation conditions described before, provision of CHO cultures with sufficient Phe prevent stagnation of product titer. Meta-Tyr supplementation showed an overall higher specific productivity qP (FIG. 4) even under Phe non-limitation conditions (FIG. 8). Supplementation of 0.1 mM, 0.3 mM, and 0.4 mM meta-Tyr under Phe non-limitation conditions increased qP compared to control by +3%, +26%, and +28%, respectively.

REFERENCE LIST

Leader B, Baca Q J, Golan D E. 2008. Protein therapeutics: a summary and pharmacological classification. Nat Rev Drug Discov 7:21-39.

Wakankar A A, Borchardt R T. 2006. Formulation considerations for proteins susceptible to asparagine deamidation and aspartate isomerization. J Pharm Sci 95:2321-2336.

Diepold K, Bomans K, Wiedmann M, Zimmermann B, Petzold A, Schlothauer T, Mueller R, Moritz B, Stracke J O, Molhoj M, Reusch D, Bulau P. 2012. Simultaneous assessment of Asp isomerization and Asn deamidation in recombinant antibodies by LC-MS following incubation at elevated temperatures. PLoS One 7:e30295.

Dengl S, Wehmer M, Hesse F, Lipsmeier F, Popp O, Lang K. 2013. Aggregation and chemical modification of monoclonal antibodies under upstream processing conditions. Pharm Res 30:1380-1399.

Li S, Schoneich C, Borchardt R T. 1995. Chemical instability of protein pharmaceuticals: Mechanisms of oxidation and strategies for stabilization. Biotechnol Bioeng 48:490-500.

Ji J A, Zhang B, Cheng W, Wang Y J. 2009. Methionine, tryptophan, and histidine oxidation in a model protein, PTH: mechanisms and stabilization. J Pharm Sci 98:4485-4500.

Hensel M, Steurer R, Fichtl J, Elger C, Wedekind F, Petzold A, Schlothauer T, Molhoj M, Reusch D, Bulau P. 2011. Identification of potential sites for tryptophan oxidation in recombinant antibodies using tert-butylhydroperoxide and quantitative LC-MS. PLoS One 6:e17708.

Khetan A, Huang Y M, Dolnikova J, Pederson N E, Wen D, Yusuf-Makagiansar H, Chen P, Ryll T. 2010. Control of misincorporation of serine for asparagine during antibody production using CHO cells. Biotechnol Bioeng 107:116-123.

Wen D, Vecchi M M, Gu S, Su L, Dolnikova J, Huang Y M, Foley S F, Garber E, Pederson N, Meier W. 2009. Discovery and investigation of misincorporation of serine at asparagine positions in recombinant proteins expressed in Chinese hamster ovary cells. J Biol Chem 284:32686-32694.

Feeney L, Carvalhal V, Yu X C, Chan B, Michels D A, Wang Y J, Shen A, Ressl J, Dusel B, Laird M W. 2013. Eliminating tyrosine sequence variants in CHO cell lines producing recombinant monoclonal antibodies. Biotechnol Bioeng 110:1087-1097.

Bridges B A. 2001. Hypermutation in bacteria and other cellular systems. Philos Trans R Soc Lond B Biol Sci 356:29-39.

Zeck A, Regula J T, Larraillet V, Mautz B, Popp O, Gopfert U, Wiegeshoff F, Vollertsen U E, Gorr I H Koll H, Papadimitriou A. 2012. Low level sequence variant analysis of recombinant proteins: an optimized approach. PLoS One 7:-e40328.

Jakubowski H. 2001. Translational accuracy of aminoacyl-tRNA synthetases: implications for atherosclerosis. J Nutr 131:2983S-2987S.

Gurer-Orhan H, Ercal N, Mare S, Pennathur S, Orhan H, Heinecke J W. 2006. Misincorporation of free m-tyrosine into cellular proteins: a potential cytotoxic mechanism for oxidized amino acids. Biochem J 395:277-284.

Hossler P, Khattak S F, Li Z J. 2009. Optimal and consistent protein glycosylation in mammalian cell culture. Glycobiology 19:936-949.

Lee S, Park J R, Seo M S, Roh K H, Park S B, Hwang J W, Sun B, Seo K, Lee Y S, Kang S K, Jung J W, Kang K S. 2009. Histone deacetylase inhibitors decrease proliferation potential and multilineage differentiation capability of human mesenchymal stem cells. Cell Prolif 42:711-720.

Murray-Beaulieu V, Hisiger S, Durand C, Perrier M, Jolicoeur M. 2009. Na-butyrate sustains energetic states of metabolism and t-PA productivity of CHO cells. J Biosci Bioeng 108:160-167.

Hendrick V, Winnepenninckx P, Abdelkafi C, Vandeputte O, Cherlet M, Marique T, Renemann G, Loa A, Kretzmer G, Werenne J. 2001. Increased productivity of recombinant tissular plasminogen activator (t-PA) by butyrate and shift of temperature: a cell cycle phases analysis. Cytotechnology 36:71-83.

Yoon S K, Choi S L, Song J Y, Lee G M. 2005. Effect of culture pH on erythropoietin production by Chinese hamster ovary cells grown in suspension at 32.5 and 37.0 degrees C. Biotechnol Bioeng 89:345-356.

Han Y K, Koo T Y, Lee G M. 2009. Enhanced interferon-beta production by CHO cells through elevated osmolality and reduced culture temperature. Biotechnol Prog 25:1440-1447.

What is claimed is:

1. A method for increasing specific productivity (qP) of a recombinant Chinese Hamster Ovary (CHO) cell that produces an exogenous polypeptide, the method comprising culturing the CHO cell in a culture medium comprising meta-tyrosine at a concentration of from 0.2 mM to 0.7 mM, whereby the specific productivity (qP) is increased by at least 5% compared to an identical culturing process without supplementation of meta-tyrosine in the culture medium.

2. The method of claim 1, wherein the eukaryotic host cell is cultured in suspension.

3. The method of claim 1, wherein the meta-tyrosine in the culture medium is at a concentration of from 0.25 mM to 0.6 mM.

4. The method of claim 1, wherein the meta-tyrosine in the culture medium is at a concentration of from 0.3 mM to 0.5 mM.

5. The method of claim 1, wherein the meta-tyrosine in the culture medium is at a concentration of from 0.3 mM to 0.4 mM.

6. The method of claim 1, wherein the culture medium further comprises phenylalanine in a non-limiting concentration.

7. The method of claim 6, wherein the molar ratio of meta-tyrosine/phenylalanine is lower than or equal to 1.25.

8. The method of claim 6, wherein the molar ratio of meta-tyrosine/phenylalanine is lower than or equal to 0.25.

9. The method of claim 6, wherein the molar ratio of meta-tyrosine/phenylalanine is lower than or equal to 0.125.

10. The method of claim 6, wherein the molar ratio of meta-tyrosine/phenylalanine is lower than or equal to 0.025.

11. The method of claim 1, wherein the exogenous polypeptide is an immunoglobulin or a variant thereof or a fragment thereof or a fusion thereof.

* * * * *